(12) United States Patent
Tapocik

(10) Patent No.: US 9,707,052 B2
(45) Date of Patent: Jul. 18, 2017

(54) MECHANICAL PEN WITH IMPROVEMENTS FOR PEN REMOVABLY RETAINING SINGLE USE CAPSULE CONTAINING TOOTH WHITENING COMPOUNDS, DENTAL BONDING COMPOUNDS AND ADHESIVES AND REMOVABLY RETAINING DISPOSABLE TOOTH WHITENING APPLICATORS, DISPOSABLE DENTAL BONDING COMPOUND APPLICATORS AND DISPOSABLE ADHESIVE APPLICATORS

(71) Applicant: Bryan Tapocik, Highland, CA (US)

(72) Inventor: Bryan Tapocik, Highland, CA (US)

( * ) Notice: Subject to any disclaimer, the term of this patent is extended or adjusted under 35 U.S.C. 154(b) by 267 days.

(21) Appl. No.: 14/609,355

(22) Filed: Jan. 29, 2015

(65) Prior Publication Data
US 2016/0220327 A1    Aug. 4, 2016

(51) Int. Cl.
| | | |
|---|---|---|
| A61C 5/00 | (2017.01) | |
| A61C 5/06 | (2006.01) | |
| A61C 19/06 | (2006.01) | |
| A61C 5/62 | (2017.01) | |

(52) U.S. Cl.
CPC .............. *A61C 5/062* (2013.01); *A61C 5/62* (2017.02); *A61C 19/066* (2013.01)

(58) Field of Classification Search
CPC .......... A61C 19/066; A61C 5/062; A61C 5/62
See application file for complete search history.

(56) References Cited

U.S. PATENT DOCUMENTS

| | | | |
|---|---|---|---|
| 4,121,739 A | 10/1978 | Devaney | |
| 5,104,005 A | 4/1992 | Schneider, Jr. | |
| 5,310,091 A | 5/1994 | Dunning et al. | |
| 5,333,760 A | 8/1994 | Simmen | |
| 5,535,922 A | 7/1996 | Maziarz | |
| 5,611,687 A | 3/1997 | Wagner | |
| 6,116,900 A | 9/2000 | Ostler | |
| 6,176,632 B1 | 1/2001 | Kageyama et al. | |
| 6,227,739 B1 | 5/2001 | Kageyama | |
| 6,283,660 B1 | 9/2001 | Furlong et al. | |
| 6,918,515 B2 | 7/2005 | Noguchi | |
| 7,201,527 B2 | 4/2007 | Thorpe et al. | |
| 7,748,980 B2 | 7/2010 | Mulhauser et al. | |
| 7,794,166 B2 | 9/2010 | Zhang | |
| 7,882,983 B2 | 2/2011 | Reidt et al. | |
| 7,980,778 B2 | 7/2011 | Akaishi et al. | |
| 8,096,449 B2 | 1/2012 | Keller | |
| 8,328,449 B2 | 12/2012 | Wightman et al. | |

(Continued)

FOREIGN PATENT DOCUMENTS

| | | |
|---|---|---|
| JP | 096151123 A | 6/1997 |
| JP | 2007130437 A | 5/2007 |

*Primary Examiner* — Amanda Patton
(74) *Attorney, Agent, or Firm* — Thomas I. Rozsa

(57) ABSTRACT

The present invention involves the field of numerous types of compounds including tooth whitening compounds and in particular, to specific apparatus which are used to retain tooth whitening compounds and then dispense them either into a dental tray where the tray is placed over the patient's teeth for a period of time or the tooth whitening compound is directly applied to the patient's teeth by the dentist or the dental assistant. More broadly described, the present invention includes compound and applicators used to dispense the compounds including tooth whitening compounds, dental bonding and filling compounds, adhesives, finely ground powder, jells, creams and paints.

16 Claims, 24 Drawing Sheets

(56) References Cited

U.S. PATENT DOCUMENTS

| | | |
|---|---|---|
| 2005/0063766 A1 | 3/2005 | Chen et al. |
| 2006/0275225 A1 | 12/2006 | Prencipe et al. |
| 2007/0086830 A1 | 4/2007 | Kageyama |
| 2008/0274066 A1 | 11/2008 | Montgomery |
| 2009/0095777 A1 | 4/2009 | Francavilla |
| 2011/0129288 A1 | 6/2011 | Uehara |

MECHANICAL PEN WITH IMPROVEMENTS FOR PEN REMOVABLY RETAINING SINGLE USE CAPSULE CONTAINING TOOTH WHITENING COMPOUNDS, DENTAL BONDING COMPOUNDS AND ADHESIVES AND REMOVABLY RETAINING DISPOSABLE TOOTH WHITENING APPLICATORS, DISPOSABLE DENTAL BONDING COMPOUND APPLICATORS AND DISPOSABLE ADHESIVE APPLICATORS

BACKGROUND OF THE INVENTION

1. Field of the Invention

This patent application contains improvements by the same inventor on co-pending utility patent application Ser. No. 14/087,401 filed on Nov. 22, 2014. The present invention relates to the field of compounds which include but are not limited to tooth whitening compounds, dental bonding and filling compounds used to fill a tooth after a cavity has been drilled out of the tooth, and adhesives used to bond two objects together, and in particular to apparatus which dispenses tooth whitening compounds used to whiten teeth, apparatus used to dispense dental bonding compounds, and apparatus used to dispense adhesives 2. Description of the Prior Art One significant problem with prior art apparatus used to retain and dispense tooth whitening compounds is that they are reused over and over, resulting in the possible transmission of diseases from one dental patient to another.

The following 26 patents and published patent applications are the closest prior art references which were uncovered in the search. A complete set of copies of these patents and patent applications are enclosed herewith for your review.

1. U.S. Pat. No. 5,611,687 issued to Eugene C. Wagner on Mar. 18, 1997 for "Oral Hygiene Delivery System" (hereafter the "Wagner Patent");

2. U.S. Pat. No. 6,176,632 issued to Hidehei Kageyama et al. on Jan. 23, 2001 for "Liquid Container" (hereafter the "'632 Kageyama Patent");

3. U.S. Pat. No. 6,227,739 issued to Hidehei Kageyama on May 8, 2001 for "Liquid Container" (hereafter the "'739 Kageyama Patent");

4. United States Published Patent Application No. 2005/0063766 to Sou Y, Chen et al. on Mar. 24, 2005 for "Applicator Pen" (hereafter the "Chen Published Patent Application");

5. U.S. Pat. No. 6,918,515 issued to Yoshio Noguchi on Jul. 19, 2005 for "Liquid Container" (hereafter the "Noguchi Patent");

6. United States Published Patent Application No. 2006/0275225 to Michael Prencipe et al. on Dec. 7, 2006 for "Applicator and Method For Applying A Tooth Whitening Composition" (hereafter the "Prencipe Published Patent Application");

7. U.S. Pat. No. 7,201,527 issued to Richard Christopher Thorpe et al. on Apr. 10, 2007 for "Twist Up Pen Type Dispenser With Brush Applicator" (hereafter the "Thorpe Patent");

8. United States Published Patent Application No. 2007/0086830 to Hidehei Kageyama on Apr. 19, 2007 for "Liquid Container" (hereafter the "Kageyama Published Patent Application");

9. United States Published Patent Application No. 2008/0274066 to Robert Eric Montgomery on Nov. 6, 2008 for "Compositions, Methods, Devices, And Kits for Maintaining or Enhancing Tooth Whitening" (hereafter the "Montgomery Published Patent Application").

10. U.S. Pat. No. 7,794,166 issued to Jun Zhang on Sep. 14, 2010 for "Press-Type Cosmetic Container with Anti-Press Means" (hereafter the "Zhang Patent");

11. United States Published Patent Application No. 2011/0129288 to Junya Uehara on Jun. 2, 2011 for "Liquid Applicator" (hereafter the "Uehara Published Patent Application");

12. U.S. Pat. No. 7,980,778 issued to Tetsuaki Akaishi et al. on Jul. 19, 2011 for "Liquid Applicator" (hereafter the Akaishi Patent");

13. U.S. Pat. No. 8,328,449 issued to James C. Wightman et al. on Dec. 11, 2012 for "Click Pen Applicator Device And Method of Using Same" (hereafter the "Wightman Patent");

14. Japanese Patent No. JP096151123A issued to Shiraishi Katsuhiko et al. on Jun. 10, 1997 for "Tooth Coating Liquid" (hereafter the "Katsuhiko Japanese Patent");

15. Japanese Patent No. JP2007130437A issued to Kageyama Shuhei on May 31, 2007 for "Liquid Container" (hereafter the "Shuhei Japanese Patent").

16. U.S. Pat. No. 4,121,739 issued to William David Devaney et al. on Oct. 24, 1978 for "Dispenser With Unitary Plunger And Seal Construction" (hereafter the "Devaney Patent");

17. U.S. Pat. No. 5,104,005 issued to Franz K. Schneider, Jr. et al. on Apr. 14, 1992 for "Dual Component Mechanically Operated Caulking Gun" (hereafter the "Schneider Patent");

18. U.S. Pat. No. 5,310,091 issued to Walter B. Dunning et al. on May 10, 1994 for "Dual Product Dispenser" (hereafter the "Dunning Patent");

19. U.S. Pat. No. 5,333,760 issued to Christen Simmen on Aug. 2, 1994 for "Dispensing And Mixing Apparatus" (hereafter the "Simmen Patent");

20. U.S. Pat. No. 5,535,922 issued to Bernard J. Maziarz on Jul. 16, 1996 for "Caulking Gun Dispensing Module For Multi-Component Cartridge" (hereafter the "Maziarz Patent");

21. U.S. Pat. No. 6,116,900 issued to Calvin D. Ostler on Sep. 12, 2000 for "Binary Energizer And Peroxide Delivery System For Dental Bleaching" (hereafter the "Ostler Patent");

22. U.S. Pat. No. 6,283,660 issued to Patrick J. Furlong et al. on Sep. 4, 2001 for "Pen Dispensing And Cartridge System" (hereafter the "Furlong Patent");

23. United States Published Patent Application No. 2009/0095777 to Frank Francavilla on Apr. 16, 2009 for "Dispensing Pen" (hereafter the "Francavilla Published Patent Application");

24. U.S. Pat. No. 7,748,980 issued to Paul Mulhauser et al. on Jul. 6, 2010 for "Dispenser for Dental Compositions" (hereafter the "Mulhauser Patent");

25. U.S. Pat. No. 7,882,983 issued to Dean K. Reidt et al. on Feb. 8, 2011 for "Capsule for Two-Component Materials" (hereafter the "Reidt Patent");

26. U.S. Pat. No. 8,096,449 issued to Wilheilm A. Keller on Jan. 17, 2012 for "Dispensing Appliance for a Multiple Cartridge" (hereafter the "Keller Patent").

The Wagner Patent discloses:

"A delivery system for a liquid oral hygiene preparation suitable for tooth whitening, tooth cleansing and the treatment of. The delivery system includes an elongate barrel shaped body. A supply of the hygiene preparation saturates a fibrous wadding carried in a hollow chamber of the body. At an end of the body, an applicator formed of felt or synthetic fibers is seated. The applicator includes a broad tip and a stem wick which is received in the wadding and draws the preparation to the tip by capillary action. The preparation is applied to tooth surfaces, oral lesions, and the like by pressing the tip against the surface to receive the preparation and, where appropriate, wiping the tip along the surface. In an alternate embodiment, ball applicator is provided and the hygienic preparation may be carried in the chamber without the wadding."

The '632 Kageyama discloses:

"A liquid container such that the liquid received in it will not easily spring out from its tip even if it is wrongly operated, comprises a tank portion for receiving a liquid, a knock bar stretching axially movably within the tank portion which is designed to have on its axial tip portion a pump shelf portion whose diameter have been enlarged, an induction bar fixed into the tip of the knock bar, a brush provided on the tip side of the induction bar, and a spring for always energizing the above knock bar and induction bar rearward. On the internal periphery surface of the above tank portion, a plurality of ribs are formed which stretch axially and on top of which the above pump shelf portion can slide, the internal periphery surface ahead of the ribs is at the same level as and continuous with the top face of the ribs and designed as a diameter-reducing portion where the pump shelf portion can slide. The pump shelf portion slidably touches the ribs when it is not biased."

The '739 Kageyama patent is related to the previously discussed patent and discloses:

"A liquid container includes a body having a tank portion housing liquid, and a liquid supply port at a front side thereof, a piston moving forward inside the tank portion, a piston rod being integrally connected to the piston and extending rearward, the piston rod having an external thread formed in a periphery thereof, an operation cylinder being attached to a rear part of the body in a relatively rotatable fashion, a piston rod guide being adapted to be rotated integrally with the operating cylinder, the piston rod guide having an internal thread hole which is engaged with the external thread of the piston rod, and a ratchet cylinder being fixed in the rear inside the body, the ratchet cylinder having a bore through which the piston rod is pierced in a relatively unrotatable fashion. The operation cylinder is formed with serrated gear teeth at a front end thereof, and the ratchet cylinder is formed with a ratchet gear tooth which is brought into engagement with the serrated gear teeth and adopted to be selectively protruded or retracted in an axial direction, at a rear end thereof."

The Chen Published Patent Application discloses:

"FIG. 1 is a cross-sectional view of an applicator pen 100 according to a first embodiment. The applicator pen 100 is formed of a number of different sub-assemblies that are then combined in an engaging manner to form the applicator pen 100. More specifically, the applicator pen 100 includes a body 110 and an applicator assembly 200 that serves to restrict and disperse an applicator material 112 that is stored within the body 110. The applicator pen 100 also includes a drive mechanism 300 for advancing the applicator material 112 within the body 110 such that it is introduced into and dispersed through the applicator assembly 200 to the consumer. The drive mechanism 300 is coupled to a button assembly 400 that permits the consumer to simply advance the applicator material 112 an incremental amount within the body 110 upon manipulation of the button assembly 400, e.g., a press and release action of the button assembly 400.

While the applicator material 112 can be any number of different types of materials, it will be appreciated that one exemplary use of the applicator 100 is as a cosmetic applicator and therefore, in this particular use, the applicator material 112 is in the form of a cosmetic product. For example, the applicator material 112 can in the form of conventional make-up, such as an eye shadow or liner, lipstick, other facial products, etc. The applicator material 112 is typically a viscous material, such as a liquid, gel or other material that has some flow properties."

The focus of this patent application is primarily a cosmetic applicator for eyeshadow, a liner, etc. and not for teeth whitening.

The Noguchi Patent discloses:

"In a liquid container, the dimension of inside diameter of a liquid supply portion is not subject to any restriction, and also a liquid leakage suppressing mechanism that is not subject to any restriction by the viscosity of stored liquid is provided. A liquid container includes a body having a tank for storing a liquid; a supply mechanism which is connected to the tip end portion of the body and has a brush for supplying the liquid; and a drive mechanism for pushing out the liquid L in the tank T to the supply mechanism. A valve which is normally closed and can be opened only when the drive mechanism is operated is provided between the tank and the supply mechanism."

The Prencipe Published Patent Application discloses:

"The dispenser 10 is shown as a complete unit in FIGS. 1 and 2. The dispenser is comprised of three sections. These are an applicator section 12, a whitening product storage section 14 and a dispenser drive section 16. The applicator section is comprised of an overcap 18, an applicator surface 30, an applicator surface holder 32, an applicator mounting unit 36 and a delivery channel 34. The whitening product in product chamber 40 is delivered to the applicator surface through delivery channel 34. A tubular wall 20 forms the product chamber 40. Piston 42 forms the upper wall of product chamber 40.

The dispenser drive section 16 is comprised of the mechanism to advance piston 42 downward in whitening product chamber 40. This dispenser drive section is shown in more detail in FIG. 5. Rotating unit 22 will rotate while tubular wall 20 of the whitening product chamber is stationary.

FIG. 7 shows an applicator tip with a fibrillated surface The applicator tip is comprised of channel 60 having a cross-section 65 which receives the peroxide containing tooth whitening composition from storage chamber 40. Fibrillated surface 62 is the application surface to apply the composition to the teeth. The peroxide tooth whitening composition flows through opening 64 of the channel 60. Applicator surface holder 66 holds channel 60 and is in turn held in place by applicator mounting unit 68. FIG. 8 is an exploded view of the applicator tip of FIG. 7. Additionally shown in this view is a chamber 70 on the applicator surface holder channel 72 of the applicator mounting unit 68. Flange 74 holds the applicator surface holder 66 in applicator mounting unit 68."

The Dwyer Published Patent Application discloses:

"A method for manufacturing a cosmetic product applicator assembly includes selecting a disposable handle having a desired design from a number of handles of various designs. Each of the handles includes an elongated, decorative housing with a first end having an opening, a hollow chamber extending from the opening into the housing, and a flattened portion for displaying a word, phrase, symbol or design. A cosmetic product applicator having a first terminal end from which the cosmetic product is dispensed and a second terminal end opposite the first terminal end is inserted into the handle. The hollow chamber is adapted to receive and engage the second terminal end of the applicator in a non-rotatable manner."

The Thorpe Patent discloses:

"As shown in FIGS. 2 and 5, the twist up pen type dispenser with brush applicator 1 comprises a body 2, preferably substantially in the shape of a cylinder, having a top 3, a bottom 4, an outer surface 5 and an inner surface 6 which defines an annular space 7. As shown in FIGS. 4 and 5, material 8 may be within the annular space 7, which functions as a reservoir for the material 8 within the twist up pen type dispenser with brush applicator 1. The material 8 may be a dentifrice, such as tooth gel, tooth paste, mouthwash, mouth rinse, tooth whitener and combinations thereof, cosmetics, such as mascara and eyeliner, hair colorants such as darkeners, like darkeners for facial hair such as moustaches, dyes or similar materials, or skin treatment compositions, combinations thereof, and the like."

The Kageyama Published Patent Application discloses:

"To provide a liquid container which includes a liquid supply member that is exchangeably mounted thereto and prevents liquids in liquid supply members from being mixed each other after exchanging the liquid supply members. The liquid container is provided which includes a container body with a tank section to hold a liquid, an applicator coupled to the front end of the container body, a piston which is advanced through the tank section, and a piston advancing mechanism which has a pushing member and causes the piston to be advanced through the tank section in response to the operation of the pushing member. The applicator is removably coupled to the container body, and the piston advancing mechanism causes the piston to be moved only forward."

The Montgomery Published Patent Application discloses:

"The first and/or second tooth whitening compositions are preferably disposed in a delivery device 10 (e.g., FIGS. 2-4, 9, and 10), such as a dispensing tube, pencil, pen or liquid stick having an applicator 12, such as a felt tip 14 (FIG. 3), brush 16 (FIG. 4), roller ball, or non-woven pad. In one embodiment, the delivery device 10 includes more than one applicator 12 that may be removably engaged with the device 10. In an embodiment wherein the device 10 is a pen or a pencil, the applicator 12 may be retractable and/or housed in a cap 18. The tooth whitening compositions of the present invention may be housed directly within a reservoir 20 in the device 10 or may be supplied in a removable cartridge (not shown) within the reservoir 20 that may be replaced or refilled. The delivery device 10 may dispense the tooth whitening composition through a transfer channel 21 through capillary action, such as in a flow through pen, or through an actuator 22, such as mechanical piston with a click mechanism, twist button and ratchet mechanism, or pushbutton mechanism, or through a vacuum method of ejection, or through other such mechanical means for transferring the composition from the device to an oral cavity surface in need of treatment. The actuator 22 may be present on first end 24 of the device 10 and the applicator on a second end 26 of the device 10 or the actuator 22 may be present on a side wall 28 of the device. In one embodiment, the delivery device 10 includes a felt tip 14 or brush 16 applicator 12 wherein the inventive composition is dispensed to the applicator 12 through actuation of the actuator 22, such as by a clicking or twisting mechanism. Kotobuke Pencil, Japan, is one manufacturer of such types of delivery devices 10 (see, e.g., U.S. Pat. No. 6,176,632)."

The Zhang Patent discloses:

"The present invention is related to a press-type cosmetic container with an anti-press means. That is, a cosmetic container adopts the way of pressing to output the material therein. More particularly, the press cover of the cosmetic container is stopped by a block to prevent discharging or leaking the material in the cosmetic container."

Claim 1 of the patent reads as follows:

"A press-type cosmetic container with an anti-press means comprising: a tube member having a sleeve at the one end thereof, the outer edge of the sleeve being disposed a collar base; a rotating tube member being disposed a female ringing slot at the inner edge of the one end thereof, the rotating tube member being female-connected to the outer edge of the sleeve and the collar base of the tube member being slid on the female ringing slot so as to make the rotating tube member be turned around on the sleeve, wherein two axial extending ribs are disposed at the inner wall of the another end of the rotating tube member, a block is disposed between the two ribs, and a resisting member is disposed beside the two ribs; a press cover having two wedging member being extended outwardly and disposed on the two side edges thereof respectively, the one end of the press cover located at the wedging member being embedded at the inner edge of the free end of the rotating tube member, and the one wedging member being disposed beyond the two ribs; herein the block stops pressing the press cover in order to stop outputting material in the cosmetic container and then achieve the function of preventing improper pressing, and the rotating tube member is then turned around, the two wedging members are moved to locations beside the resisting member so as to output the material."

The Uehara Published Patent Application discloses:

"The present invention is a liquid applicator which, in its assembled state an applying part, joint, and front barrel are fixed to a barrel body front end portion, the step of an indented/projected engaging portion on the inner peripheral side of the applying part rear end portion is abutted from behind against and engaged with the step of an indented/projected engaging portion on the outer peripheral side of the forward part of the joint. At the same time, an indented/projected engaging portion on the outer peripheral side of the applying part rear end portion is abutted against and engaged with an indented/projected engaging portion on the inner peripheral side of the front barrel's forward part, and an indented/projected engaging portion on the inner peripheral side of the front barrel rearward part is engaged with an indented/projected engaging portion on the outer peripheral side in the rearward part of joint, whereby applying part, joint and front barrel are formed so as to fix the applying part to barrel body by means of the joint and the front barrel."

The Akaishi Patent discloses:

"A liquid applicator includes a liquid pressing mechanism 6 for pressurizing an application liquid 4 inside a main body 2 so as to supply the application liquid to an applying member 10 at the front end by the pressing of liquid pressing mechanism 6, wherein the applying member 10 is made of an elastic material, has a valve structure 8 which is formed with a communication path 24 for communication between the inside and outside of main body 2 and can close the communication path 24 by elasticity in the normal condition and open the communication path 24 by elastic deformation of the communication path when the application liquid is pressurized by liquid pressing mechanism 6, and, an ejection opening 24a of communication path 24 of valve structure 8 is arranged to front onto the applying portion 10a of the applying member 10."

The Wrightman Patent discloses:

"A click pen applicator device that provides predetermined dosing of the formulation for precise application, and rapidly primes the formulation using the dosing click mechanism to prepare the applicator for use."

Claim 1 of the patent reads as follows:

"A device for dispensing a formulation comprising: a centerband having a proximal end and a distal end and defining a storage section having the formulation disposed within; an applicator section situated at the distal end of the centerband; and a multistage actuator section situated at the proximal end of the centerband for rapid priming with a click dispensing mechanism with a piston seat having two sets of external threads on a shaft with an unthreaded length therebetween."

The Katsuhiko Japanese Patent discloses:

"PROBLEM TO BE SOLVED: To obtain a coating liquid capable of coloring tooth or tooth crowns to white or any other color by using an acrylic resin prepared by neutralizing an acrylic ester-methacrylic eater-based copolymer with a specific compound. SOLUTION: This tooth coating liquid contusions ethanol and an acrylic resin prepared by neutralizing an acrylic ester-methacrylic ester-based copolymer with 2-amino-2-methyl-1,3-propanediol or 2-amino-2-methyl-1-propanol, and may also contain a color pigment or extender pigment, and furthermore, ceramic(s) and/or a vinyl acetate resin. It is preferable that this coating liquid comprises 10-94.8 wt. % or more of ethanol, 0.1-30 wt. % of a pigment, 0.1-20 wt. % of the above acrylic resin, and 5-30 wt. % of ceramic(s) and/or butyl acetate resin. The pigment is pref. titanium dioxide (optimally, 100 nm primary particle diameter on average)."

The Shuhei Japanese Patent discloses:

"PROBLEM TO BE SOLVED: To provide a liquid container which includes a liquid supply member that is exchangeably mounted thereto and prevents liquids in liquid supply members from being mixed each other before and after exchanging the liquid supply members. SOLUTION: The liquid container includes a container body 12 with a tank section T to hold a liquid, an applicator 20 coupled to the front end of the container body 12, a piston 22 which is advanced through the tank section T, and a piston pressing mechanism 23 which has a knocking member 32 and causes the piston 22 to be pressed through the tank section T in response to the operation of the knocking member 32. The applicator 20 is removably coupled to the container body 12, and the piston pressing mechanism 23 causes the piston 22 to be moved only forward."

The Devaney Patent discloses:

"A dispenser for precisely metering viscous fluids from a cartridge. The dispenser includes a cartridge body and a plunger having a piston head at its extremity. The plunger is unitarily configured from a plastic material, including seal rings in the piston head. Each piston head including two such seal rings axially spaced from one another and configured to include sharp peripheral edges permitting resilient wedging contact within the bore of the cartridge."

The Schneider Patent discloses:

"A dual component caulking gun which utilizes a gun body to which there is affixed a dual component cartridge assembly designed to carry dual component cartridges. A ball screw is journaled within the gun body for rotary motion but locked against axial motion and extends in a direction opposite the component cartridge assembly. A pair of ram rods are journaled through the gun body and terminate at the first end in ejector rams and at their opposite end in a transfer bar that is interconnected to the ball screw by means of a ball screw nut."

The Dunning Patent discloses

"A dispenser for simultaneously dispensing and mixing a pair of fluid products such as chemically reactive resins, from a pair of axial adjacent front and rear chambers. A piston is mounted within each of the chambers and is moveable with respect to the hollow interior of the respective chamber for dispensing the fluid product therefrom. Telescopic movement of the rear chamber within the front chamber moves the pistons synchronously through the chambers to provide for controlled discharge of the products through a front discharge nozzle. A fixed hollow delivery tube extends through the interior of the front chamber and telescopically receives therein a post which is mounted on a rear wall of the rear chamber. The rear chamber has a relatively tight sliding fit within the front chamber so that a partial vacuum is formed within an annular space which forms between the two pistons as they move apart upon discharge of the two products to produce a "suck back" effect on product remaining in the discharge nozzle."

The Simmen Patent discloses:

"A dispensing and mixing apparatus for simultaneously dispensing from a cartridge into a static mixing element components which harden when mixed. The components exit the cartridge into the mixing element without intermixing as the components leave the cartridge. The initial intermixing of the components takes place within the mixing element. The cartridge is reusable since the components do not become mixed and harden as they come out of the cartridge. The chambers in the cartridge are of semi-cylindrical configuration and have rounded corners. Ribs can be provided on the cartridge for stiffening the cartridge from deforming under extrusion."

The Maziarz Patent discloses:

"The invention provides a dispensing module for dispensing multi-part adhesive from a multi-component cartridge utilizing a standard caulking gun. The dispensing module comprises a piston actuator and a module housing which when assembled with a standard multi-component cartridge and inserted into a standard caulking gun allows the components from the multi-component cartridge to be dispensed."

The Ostler Patent discloses:

"A dental bleach storage, mixing and delivery device and related method are disclosed. The device includes a barrel with at least two chambers. The chambers store components that when mixed can form a dental bleach or whitener. A plunger is provided that can be reciprocated within the barrel to force such components from their chambers. A mixing tip is provided for the end of the barrel. The components may be forced through the mixing tip which thoroughly mixes them together. The resulting bleach or whitener is applied to a patient's teeth where oxygen ions released from the bleach or whitener and will whiten the patient's teeth."

The Furlong Patent is a pen dispensing cartridge system which issued in 2001 and is still in full force and effect. The patent discloses:

"The present invention features a pen used, for example, to dispense nail polish for finger nail application. The design is for a unit of use, meaning that the preferred pen uses cartridges, i.e., units. In a preferred embodiment, each cartridge is filled with polish and has a brush head. After the cartridge is used, the user simply disposes of the old cartridge and replaces it with a new cartridge for the next application."

The Francavilla discloses:

"The present invention is related to a dispensing device. The dispensing device includes a container; a dispensing opening located at one end of the container; a plunger located inside the container; a pushbutton associated with the plunger; and a drive mechanism configured to drive the plunger linearly inside the container from a first position towards the dispensing opening when the pushbutton is pressed and to hold the plunger at a second position, wherein the second position is closer to the dispensing opening than the first position."

The Reidt Patent discloses:

"Capsule (10) for two or more components of a material which are to be mixed together, comprising a cartridge (11) comprising an outlet (12), a first component chamber (13) for containing a first component, and a second component chamber (14) for containing a second component, the two chambers (13, 14) opening into the outlet (12); and a piston (15) which at least with its front end sits in the cartridge (11), lies with its rear end outside the component chambers (13, 14) and, when it is pushed forwards, presses the two components out of their component chambers (13, 14)."

The Mulhauser Patent discloses a dispenser for dental compositions.

Claim 1 of this patent reads as follows:

"An apparatus for dispensing dental compositions, the apparatus comprising: a) a body comprising a top shell portion, a bottom shell portion, and a chamber received therein; b) a replaceable cartridge having at least two lumens with at least two pistons, the cartridge operable to dispense a component of a dental compound contained within the lumens, and wherein the cartridge is further operable to be at least partially inserted into the chamber; c) an inner mechanical system disposed in the body, the inner mechanical system comprising a rack system, said rack system having at least two racks operable to be urged forward to engage a piston in each lumen of the cartridge; d) a button system in contact with the body, the button system operable to be depressed in a direction substantially forward and in line with the rack system by a user such that the button system engages the inner mechanical system when depressed, such that the rack is advanced a predetermined distance such that a metered amount of the components of the dental compound is dispensed from the at least two lumens; and e) wherein the inner mechanical system further comprises a plurality of teeth disposed on the rack system, and a drive spring and a pawl spring disposed on the body, the drive spring and the pawl spring being operable to interface with at least one of a plurality of teeth on the rack system and at least one surface of the button system such that depression of the button system by a user initiates drive spring to advance the rack system a predetermined distance proportional to the distance between a first selected tooth located on the rack and a second selected tooth located on the rack and initiates the pawl spring to disengage from a third selected tooth on the rack and engage a fourth selected tooth on the rack located at a distance substantially equal to the distance between the first tooth and the second tooth, and release of the button causes the drive spring to disengage from said first selected tooth and engage the second selected tooth on the rack."

The Keller Patent discloses a dispensing appliance for a multiple cartridge. The broadest claim is Claim 1 which reads as follows:

"A dispensing appliance for a multiple cartridge or syringe, comprising: a housing configured to receive the multiple cartridge or syringe, and wherein the housing has a housing thread and a rotatable portion that has a complementary thread, wherein the housing thread and the rotatable portion cooperate in such a manner that by a mutual rotation of the housing thread and the rotatable portion, the rotatable portion is continuously displaceable relative to the housing in a dispensing direction, wherein the housing is configured to receive the multiple cartridge or syringe having at least two adjacent and parallel storage containers, wherein a thrust force of the rotatable portion is transmitted to a multiple ram with a single thrust plate, and wherein the multiple ram slides in the at least two adjacent and parallel storage containers of the multiple cartridge or syringe and the thrust plate is non-rotatably guided inside the housing."

There is a significant need for an improved apparatus to dispense compounds including but not limited to tooth whitening compounds where the tooth whitening compounds are dispensed from a new and unused retainers. There is also a significant need for an improved apparatus to dispense dental bonding compounds from new and unused retainers and adhesive compounds from new and unused retainers.

SUMMARY OF THE INVENTION

The present invention involves the field of numerous types of compounds which by way of example includes tooth whitening compounds and in particular, to specific apparatus which are used to retain tooth whitening compounds and then dispense them either into a dental tray where the tray is placed over the patient's teeth for a period of time or the tooth whitening compound is directly applied to the patient's teeth by the dentist or the dental assistant. More broadly described, the present invention includes compounds and applicators used to dispense the compounds including tooth whitening compounds, dental bonding and filling compounds, adhesives such as glue, finely ground powder, jells, creams, paints, cosmetics, lipstick, non-medicated cosmetics, medicated cosmetics, construction material compounds, and virtually any substance that has a sufficient viscosity to be pushed through a dispensing cartridge in a dispensing pen and either out of the cartridge, from the cartridge into an applicator, or from the cartridge into a mixing chamber and then out of the mixing chamber primarily into an applicator, which are hereafter jointly referred to in this patent application as "compounds".

The cartridges have either a single interior chamber or two interior chambers where the dual or two chambers are separated by a dividing wall. For a compound that does not require mixing, a single compound in a single interior chamber cartridge is used. Where two compounds are divided and only mixed immediately before use, the dual interior chamber cartridge is used.

Although the summary discussed below relates to tooth whitening compounds in detail, it is understood that the present invention includes all products defined above as compounds and is not limited to tooth whitening compounds.

The present invention involves a dispensing pen which removably retains a single use capsule containing tooth whitening compound and removably retains disposable tooth whitening applicators. One of the major problems with prior art tooth whitening applicators is that the applicator itself is reused over and over again through syringes which contain the tooth whitening compound and even though they are sterilized, run the risk of transmitting disease from one patient to another. Therefore, there is a significant need for an improved tooth whitening apparatus where the capsule containing the tooth whitening compound or compounds is disposable and replaceable with a new clean capsule with a fresh supply of tooth whitening compound or compounds and the applicator heads which are used to apply the compounds to teeth or to a dental tray are also disposable and replaced with new applicators so that the patient receives a completely new and sterile system for the purpose of applying tooth whitening compounds. The only portion of the apparatus which is reused is the retaining pen which is used to removably retain the tooth whitening compound and to removably retain the tooth whitening applicators.

The variations of the embodiments of the present invention involve two variations on the interior of the single use capsule. The variations of the embodiments of the present invention also involve the location of the single use capsule.

In one embodiment of the present invention, the interior chamber of the unidose single use cartridge or capsule contains tooth whitening compound in a sealed condition with a cap that has an openings which is sealed by a frangible opening which seals the capsule until it is ready for use and a screw on cap which contains at a remote end a piercing object to pierce the frangible seal so that the tooth whitening compound can be dispensed from the capsule. In one variation, the capsule or cartridge has a single interior chamber so that the tooth whitening compound does not require any mixing before the tooth whitening compound is dispensed from the capsule or cartridge (capsule and cartridges are used and referred to interchangeably). For this variation, the rear of the interior chamber of the capsule or cartridge contains a single plunger having a pair of spaced apart sidewalls forming a seal against the interior sidewall of the cartridge. The rear of the plunger also includes a single pocket which receives a pushing piston from the retaining pen, the pushing piston is moves in a forward direction within the pen by an improved ratchet mechanism of the present invention. The pushing piston engages and pushed the single pocket in the rear of the single plunger to push the compound out of the cartridge through an opening in a front nozzle of the capsule after a seal on the nozzle is opened. In one sub-variations of this embodiment, the cartridge is retained within an interior chamber of the pen with the nozzle extending through a front opening in the pen. In another sub-variation, the pen has a threaded exterior sidewall with male threads adjacent the front of the pen and the cartridge has mating interior female threads by which the cartridge is threaded onto the front of the pen and extends from the front of the pen and is exterior to the pen. The is still a similar sealing configuration on the rear of the cartridge which the single piston pushing against the single pocket in the sealing plunger which now extends out of the pen into the exterior cartridge. The same new and novel ratch mechanism pushes the piston in increments to push the plunger which pushes the whitening compound out of the opening in the nozzle.

In an alternative embodiment of the present invention, the interior chamber of the unidose single use cartridge or capsule also contains tooth whitening compound in a sealed condition with a cap that has an openings which is sealed by a frangible opening which seals the capsule until it is ready for use and a screw on cap which contains at a remote end a piercing object to pierce the frangible seal so that the tooth whitening compound can be dispensed from the capsule. In the alternative variation, the capsule or cartridge has an interior longitudinal dividing wall with separate tooth whitening compounds in each chamber bounded by an interior surface of the cartridge and the dividing wall. The divided interior chamber retains two separate compounds which are separated from each other while in the cartridge by the a dividing wall. The interior rear of the cartridge has a different plunger having opposing interior faces to push a compound in a respective portion of the interior of the cartridge forward and out of the cartridge, and a pair of opposed angular sidewalls ending in rear wall sidewalls forming a seal against the interior sidewall of the cartridge. Each rear end of the plunger has a pocket to receive a respective pushing piston from a dual piston mechanism in the retaining pen. The interior chamber is divided into two equal chambers which contain different compounds which cannot come in contact with each other because the dividing wall extends for the entire diameter and length of the interior chamber of the cartridge. For dual compounds where less is need of one of the two compounds, the dividing wall is thicker on one side to reduce the volume of compound in the smaller chamber, the design of the plunger is modified to accommodate the revised sidewall. For the operating mechanism for the dual chamber cartridge, the mechanism includes a pair of pistons which are respectively used to engage a respective pocket of the two-pocket plunger used with the dual chamber cartridge and a ratchet mechanism to incrementally move each pushing piston in a forward direction within the pen by an improved ratchet mechanism of the present invention. The pushing pistons respectively engage and push a respective one of the two pockets in the rear of the dual plunger to push the compounds out of the cartridge through an opening in a front nozzle of the capsule after a seal on the nozzle is opened. After the compounds are pushed out of the cartridge, they are mixed in ax a mixing chamber before being dispensed. In one sub-variation of this embodiment, the cartridge is retained within an interior chamber of the pen with the nozzle extends through a front opening in the pen. In another sub-variation, the pen has a threaded exterior sidewall with male threads adjacent the front of the pen and the cartridge has mating interior female threads by which the cartridge is threaded onto the front of the pen and extends from the front of the pen and is exterior to the pen. The is still a similar sealing configuration on the rear of the cartridge which the dual pistons respectively pushing against a respective one of the two pockets in the sealing plunger which now extends out of the pen into the exterior cartridge. The same new and novel ratch mechanism pushes the pistons in increments to push the plunger which pushes the whitening compound out of the opening in the nozzle into the mixing chamber.

The additional significant improvement is the new sand novel ratchet mechanism which mechanically pushes the single piston or dual pistons in increments to push a plunger in increments to dispense a desired amount of compound.

After the compound, whether single or mixed dual is dispensed, it extends to an applicator. With respect to alternative embodiments of the applicators, one embodiment is a straight applicator which is generally frustum shaped having a narrow dispensing tip and a threaded end which is threaded onto either the threaded end of the mixing tip or a threaded end of the cartridge and through which the tooth whitening compound flows and can be placed either into a dental tray or onto a patient's teeth.

In an alternative embodiment of the applicator, the applicator is horn-shaped or bent so that the tooth whitening can be directly applied to locations in the patient's mouth where teeth are near the back of the mouth, either upper or lower teeth and usually on the exterior but if necessary, also on the top or interior of the tooth.

In an alternative embodiment of the applicator, the applicator has an opening with a brush so that the tooth whitening compound extends through the applicator opening and then the brush is used to apply the tooth whitening compound onto the patient's tooth.

It is a primary object of the present invention to provide a reusable capsule and reusable applicator so that tooth whitening compounds which are contained in the capsule are used only once and the applicators used to apply the tooth whitening compound are also used only once and then discarded and replaced with a separate tooth whitening compound retaining capsule or cartridge and also replaced with separate applicator heads.

It is a further object of the present invention to provide a single use cartridge or capsule which contains a single compound which does not need to be mixed with any other compound and can simply be dispensed once the sealed capsule or cartridge is opened to dispense the tooth whitening compound onto teeth or onto a dental tray where it can be used.

It is a further object of the present invention to provide a single use capsule which has a dividing wall so that the capsule contains two separate compounds which are separated from each other and which may either have equal amounts of compounds on either side of the dividing wall or different amounts of compound where one compound is less than the other compound depending upon the formulation required for that tooth whitening application and then the compounds are mixed when they enter a chamber for mixing purposes.

It is the primary object of the present invention to provide a non-reusable container and non-reusable applicator head so that a fresh container containing fresh tooth whitening compounds, fresh dental bonding and filling compounds and adhesive compounds and fresh new applicators are used every time a new compound is dispensed so that a compound is not reused from one patient to another or from one adhesive bonding application to another, thereby providing safety and health to subsequent patients and products.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The variations on the single use cartridges have been summarized in detail in the summary of the invention section. The cartridge variations are summarized as follows:

(1) a single use cartridge having a single interior chamber housing a compound. This variations has two sub-variations: (a) the single use cartridge is within a chamber within the mechanical dispensing pen with a nozzle extending out of an opening in the dispensing pen; and (b) the single use cartridge is threaded onto threads adjacent the opening of the mechanical dispensing pen and is outside of the dispensing pen. In both sub-variations, the nozzle from the single use cartridge is threaded onto an applicator or brush.

(2) A single use cartridge having a double interior chamber divided by a dividing wall so that a respective compound is in each separate chamber of the dual chamber single use cartridge. This variations also has the same two sub-variations: (a) the single use cartridge is within a chamber within the mechanical dispensing pen with a nozzle extending out of an opening in the mechanical dispensing pen; and (b) the single use cartridge is threaded onto threads adjacent the opening of the dispensing pen and is outside of the dispensing pen. In both sub-variations, the nozzle from the single use cartridge is threaded onto a mixing chamber where the two compounds are mixed after being dispensed from the single use cartridge, and the mixing chamber has a nozzle which is threaded onto an applicator or brush after the mixing process. These variations and sub-variations will be described after discussion of the new innovations in this invention.

The variations are all utilized with the innovative new mechanical ratchet mechanism for advancing the piston within the dispensing pen to push against a pocket in a sealing plunger located adjacent the interior rear of the single use cartridge. For the variation where the single use cartridge has one chamber, the sealing pushing plunger has one pocket to receive one pushing piston. For the variation where the single use cartridge has a dual chamber, the sealing pushing plunger has two pockets to respectively receive a respective one of the dual pushing pistons to push a respective half of a the sealing plunger to dispense each respective compound. In either variation, the new and novel ratchet mechanism to push either a single or dual pushing piston is the same.

Figure 1:
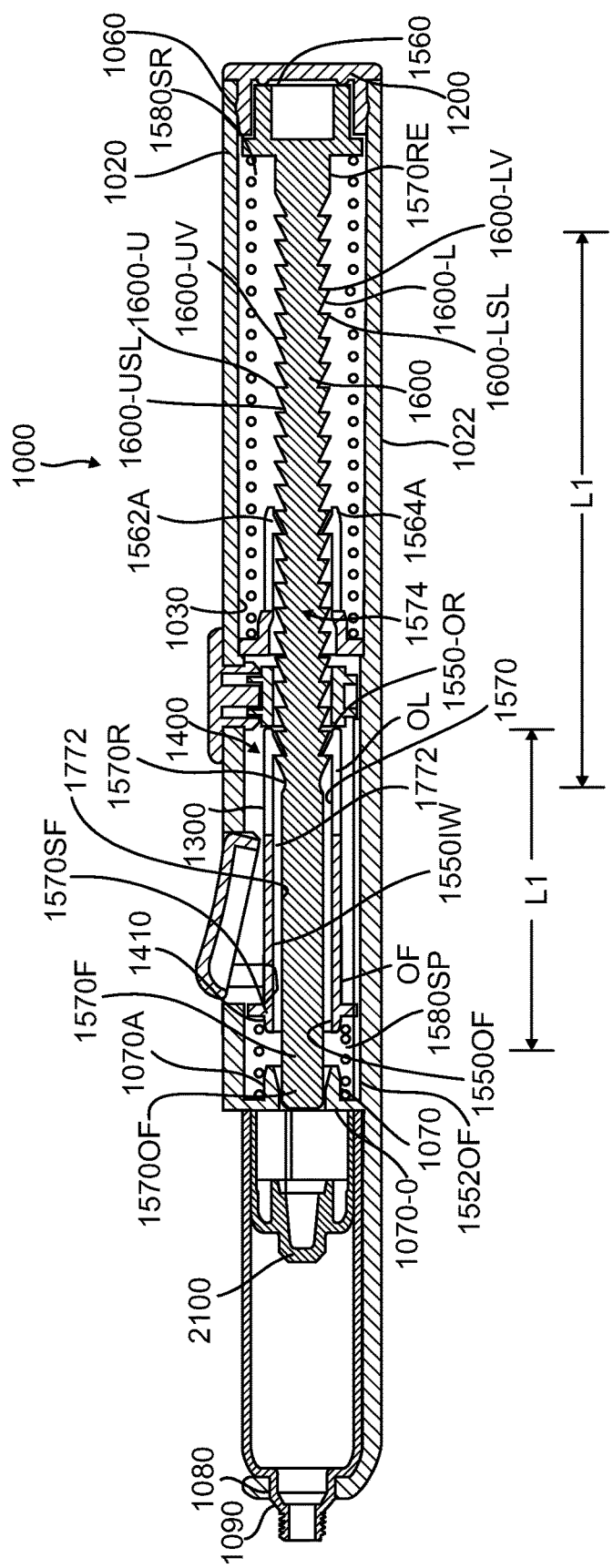
FIG. 1 is a cross-sectional view of the dispensing pen which retains a single use cartridge within the dispensing pen and further discloses the new and novel mechanical ratchet mechanism of the present invention.
Figure 2:
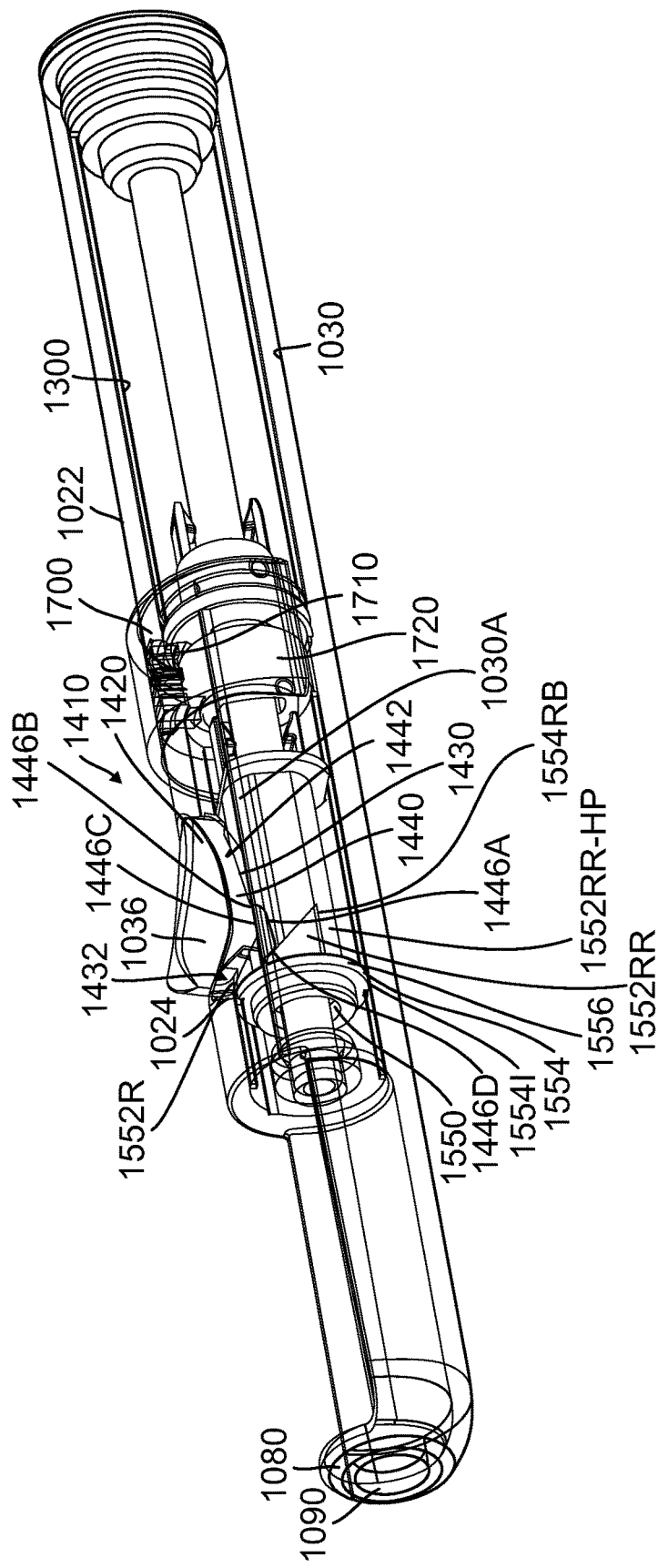
FIG. 2 is a top left perspective view of the dispensing pen with the dispensing pen illustrated in a transparent exterior to enable illustration of a portion of the opera+ting mechanism of the new and novel mechanical ratchet mechanism.
Figure 3:
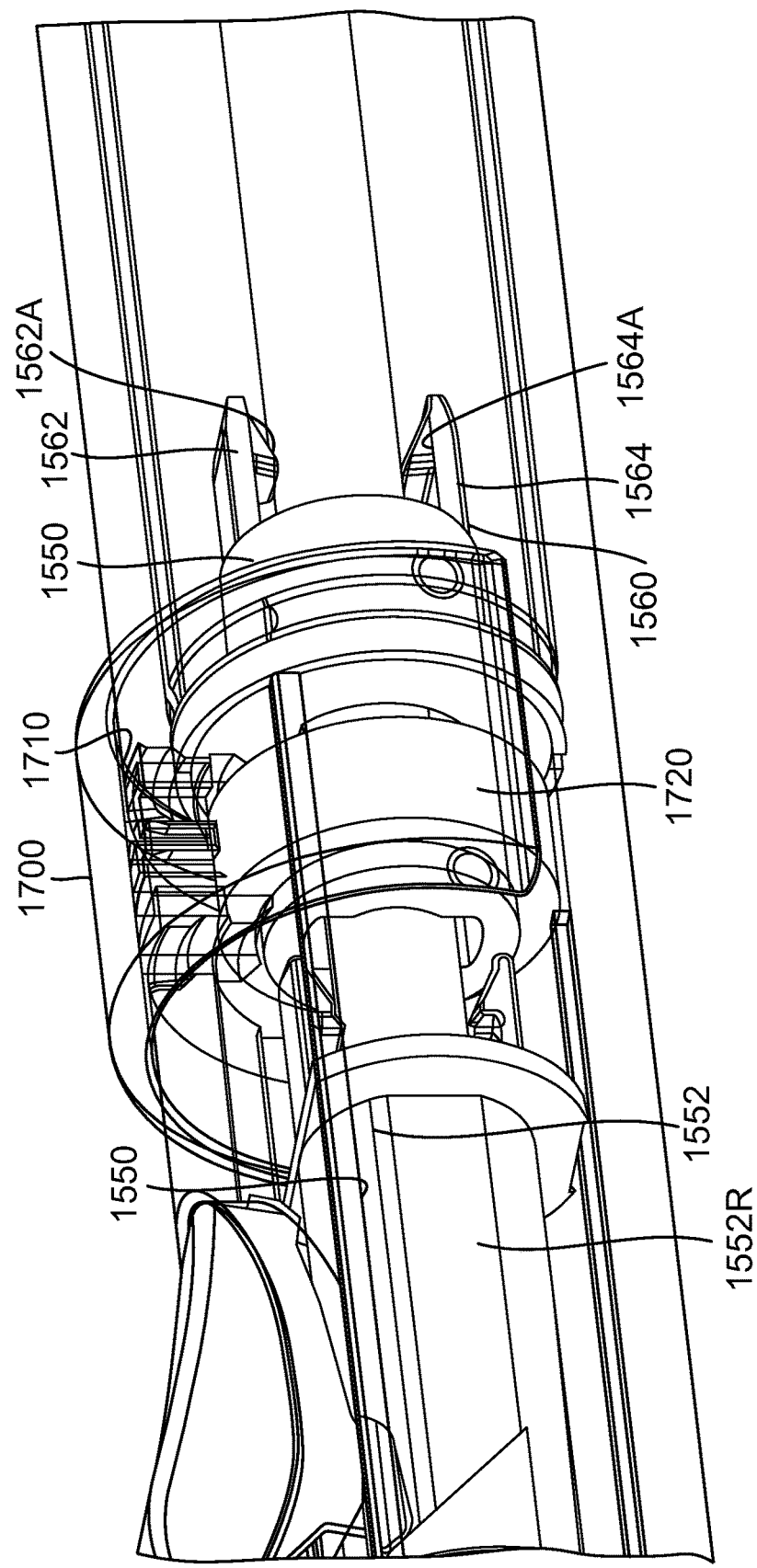
FIG. 3 is a top left enlarged perspective view of a section of the dispensing pen with the enlarged section of the dispensing pen illustrated in a transparent exterior to enable illustration of an enlarged portion of the operating mechanism of the new and novel mechanical ratchet mechanism.
Figure 4:
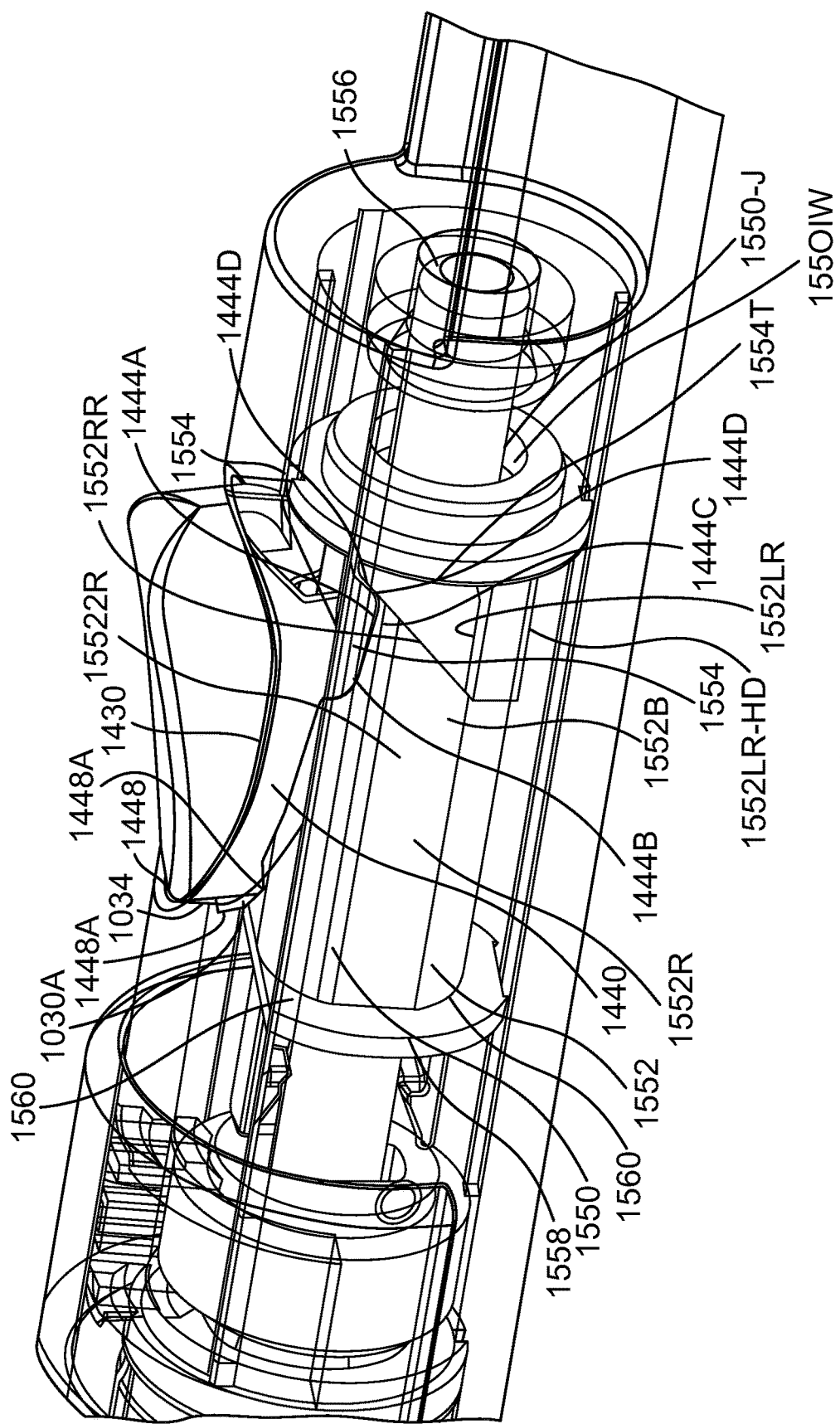
FIG. 4 is a top right enlarged perspective view of a section of the dispensing pen with the enlarged section of the dispensing pen illustrated in a transparent exterior to enable illustration of an enlarged portion of the operating mechanism of the new and novel mechanical ratchet mechanism.
Figure 5:
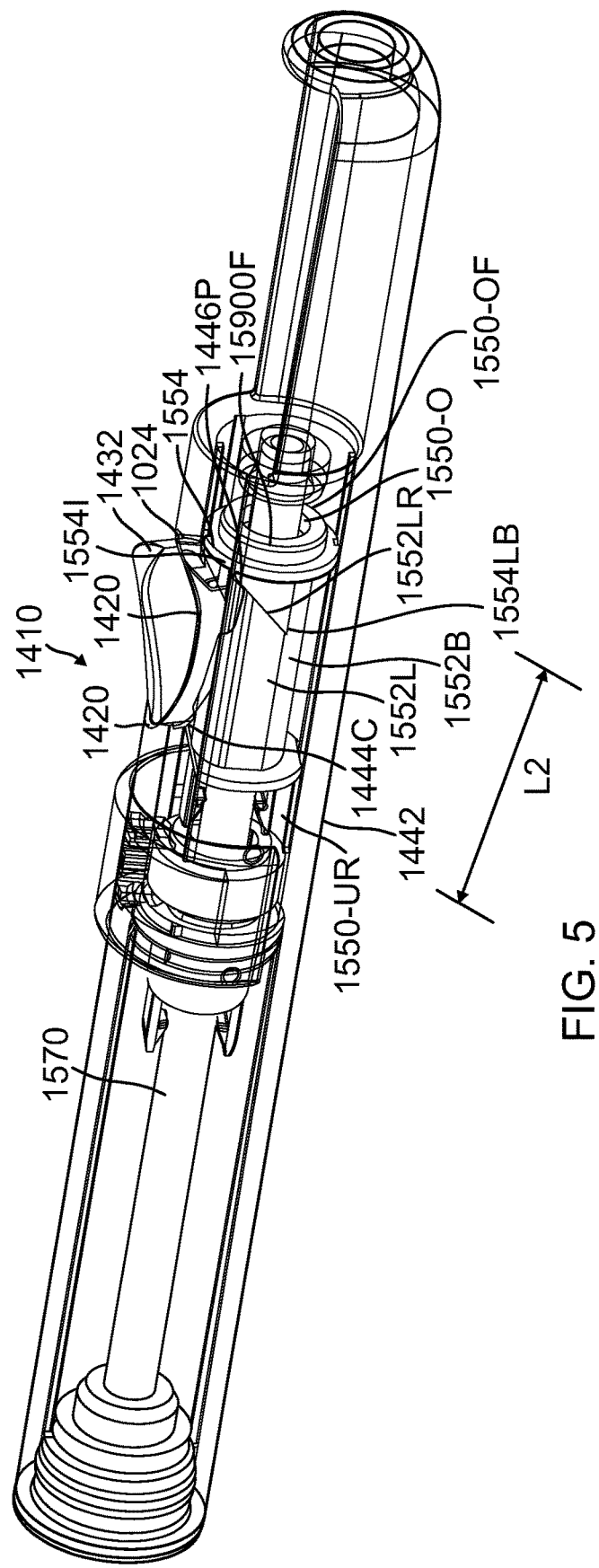
FIG. 5 is a top right perspective view of the dispensing pen with the dispensing pen illustrated in a transparent exterior to tenable illustration of a portion of the opera+ting mechanism of the new and novel mechanical ratchet mechanism.

The dispensing pen has two variations, one where there is an interior chamber to receive the single use cartridge within the dispensing pen. This variation will be described first. FIG. 1 is a cross-sectional view of the dispensing pen 1000 which retains a single use cartridge 10A within the dispensing pen. A cross-sectional view of the new and novel ratchet mechanism 1100 is disclosed in the cross-sectional view of FIG. 1. FIG. 2 is a top left perspective view of the dispensing pen with the dispensing pen illustrated in a transparent exterior to enable illustration of a portion of the operating mechanism of the present invention. FIG. 3 is a top left enlarged perspective view of a section of the dispensing pen with the enlarged section of the dispensing pen illustrated in a transparent exterior to enable illustration of an enlarged portion of the operating mechanism of the present invention. FIG. 4 is a top right enlarged perspective view of a section of the dispensing pen with the enlarged section of the dispensing pen illustrated in a transparent exterior to enable illustration of an enlarged portion of the operating mechanism of the present invention. FIG. 5 is a top right perspective view of the dispensing pen with the dispensing pen illustrated in a transparent exterior to enable illustration of a portion of the operating mechanism of the present invention.

Referring to FIGS. 1 through 5, the dispensing pen 1000 has a circumferential wall 1020 with an exterior surface 1022 and an interior surface 1030 (See FIG. 2). The dispensing pen 1000 has an open rear end 1060 covered by a sealing cap 1200. The dispensing pen has a front end wall 1080 with a front end opening 1090 extending from the front end wall 1080. The interior surface 1030 and sealing cap 1200 surrounds an interior chamber 1300 which retains the ratchet operating mechanism 1400 which is comprised of the following components. An operating pushbutton 1410 which has a rear end 1420 and an arcuate lower surface 1430 about which the operating pushbutton 1410 pivots. The circumferential wall 1020 of the dispensing pen 1000 has an opening 1024 through which the front end 1432 and top surface wall 1436 of the operating pushbutton 1410 extend. Referring to FIG. 5, the lower arcuate surface 1430 of the operating pushbutton 1410 rests on a pushbutton connection base 1440 having a seat 1442 on which the lower arcuate surface 1430 pivots. The pushbutton connection base 1440 (See FIG. 2) has a first foot 1444A (see FIG. 4) extending from a width-wise first front and underside member 1444B, the first foot member 1444A has a longitudinal body 1444C terminating in a slanted front face 1444D and a parallel oppositely disposed second foot 1446A extending from a width-wise second front and underside member 1446B, the second foot member 1446A has a longitudinal body 1446C terminating in a slanted front face 1446D. The pushbutton connection base 1440 has a rear end 1448 (see FIG. 4) with a longitudinal pivot member 1448A (see FIG. 2) extending away from the rear end and against an interior location 1030A of interior wall 1030 which serves as a connection point for the pushbutton connection base 1440.

Beneath the pushbutton connection base 1440 is a longitudinal slide member 1550 having a longitudinal exterior surface 1552 with a first circumferential stop member or ring 1554 (see FIG. 2) encircling the longitudinal exterior surface 1552 at a spaced apart location from the front 1556 of the longitudinal slide member 1550. A rear circumferential stop member or ring 1558 located at a rear end 1560 of the longitudinal slide member 1550 (see FIG. 4) and including an upper shaft holder 1562 (see FIG. 3) extending away from the rear end 1560, the upper shaft holder having a downwardly extending clip 1562A; a lower shaft holder 1564 extending away from the rear end 1560 and having an upwardly extending clip 1564A The longitudinal exterior surface 1552 has a first or right flatted sidewall 1552R with a first or right ramp 1552RR extending from an interior surface section 1554I of first circumferential stop ring 1554 to adjacent a bottom longitudinal portion 1554RB of the right flattened sidewall 1552R and a second or left flattened sidewall 1552L with a second or left ramp 1552LR extending from an interior surface section 1554I of first circumferential stop ring 1554 to adjacent a bottom longitudinal portion 1552LB of the left flattened sidewall 1552L.

The longitudinal slide member 1550 includes an interior longitudinal generally cylindrical opening 1550-O extending for the entire length "L1" of the longitudinal slide member 1550 and bounded by a longitudinal interior circumferential wall 1550IW, and open at its front end 1550-OF and open at its rear end 1550-OR. A multi-section shaft 1570 has a smooth outer surface section 1772 which extend through the entire length of the interior longitudinal generally cylindrical opening 1550-O and for a given distance beyond the open front end 1550-OF adjacent a front interior wall 1070 has a cylindrical supporting arm 1070A extending interiorly toward the longitudinal side member 1550, and having a central opening 1070-O which receives and supports a front end 1570F of shaft 1570. A first compression spring 1580SP is supported by cylindrical supporting arm 1070A at a front end and by a front section 1570SF of the slide member 1570, the slide member having a front cylindrical exterior separation wall which separates the rear of the first compression spring 1580SF from the pushbutton 1410 when it is depressed.

The second section 1574 of the multi-section shaft 1570 has a multiplicity of adjoining ratchet teeth 1600 extends from a given distance "L2" behind the opening at the rear end 1570-OR of slide member 1570 to adjacent a rear multi-section end 1570-RE of the multi-section shaft 1570. The rear end 1570-RE ends in a solid plug member 1560 which in turn in received in and supported by sealing cap 1200. Each individual ratchet tooth is in the shaped of an isosceles triangle beginning with a sloped side and extending at an upward slant to a rear end for a shot straight edge of the triangle, a second section 1574 serving as the long straight edge of the triangle. The triangles are formed as identical mirror images of each other at a same location of the second section 1574 and respectively above and below the second section 1574. Each ratchet tooth above the second section 1574 is referred to as an upper ratchet tooth 1600-U with an upper vertical wall 1600-UV and an upper forwardly slanted surface 1600-USL. Each ratchet tooth below the second section 1574 is referred to an a lower ratchet tooth 1600-L with a lower vertical wall 1600-LV and a lower forwardly slated surfaced 1600-LSL.

A second or rear compression spring 1580SR extends around all of the multiplicity of ratchet teeth 1600 and is retained at a rear end on the solid plug member 1060 and retained on a front end is retained on upper shaft holder 1562 and on lower shaft holder 1564.

In operation, the novel and unique improved mechanical ratchet operating mechanism 1400 is operated as follows. The first compression spring 1580SP and the second compression spring 1580SR are in their uncompressed state. The operating pushbutton 1410 is elevated in the uncompressed state. The downwardly extending clip 1562A rests on an uppermost portion of an upper forwardly slanted surface 1600-USL adjacent a vertical wall 1600-UV of an upper ratchet tooth 1600-U and an upwardly extending clip 1564A rests on a lowermost portion of a lower forwardly slanted surface 1600-LSL adjacent a lower vertical wall 1600-LV of a lower ratchet tooth 1600-L To begin the process of moving the multi-section shaft 1570 incrementally forward by a ratchet step (as will be described the front end 1570F is connected to a single or double piston which pushes a sealing plunger in a cartridge forward to push the compound or compounds within the cartridge forward and eventually out of the cartridge), the operating pushbutton 1410 is pressed downwardly by pushing top surface wall 1436 adjacent a front location 1432 of the top surface wall 1536 towards the slide member 1570. In this process, the downwardly pressed pushbutton 1410 causes its arcuate lower surface 1436 to pivot causing pushbutton connection base 1440 to move in the same downward direction which in turn causes slanted front faces 1444D and 1446D of the respective first foot member 1444A and second foot member 1446A to respectively slide down right ramp 1552RR and left ramp 1552LR of slide member 1550. When the operating pushbutton 1410 is fully pressed all the way down, the first and second foot 1444A and 1446A of the pushbutton connection base 1440 have respectively slid down ramps 1552RR and 1552LR which caused the slide member 1570 to move forwardly by the horizontal distance of the ramps (1552RR-HD and 1552LR-HD). This in turn compresses first compression spring 1580SP and advances the multi-section shaft 1570 forward by the a horizontal distance of a tooth (1600-U and 1600-L) which in turn compresses second spring 1580SR. When the operating pushbutton is released, the clips 1662A and 1664A have slid down a respective slanted surface 1600-USL and 1600-RSL and respectively stop at the next vertical wall 1600RV and 1600-LV of a ratchet and holds the multi-sectioned shaft 1570 from moving backward. The slide member 1570 moves backwards due to the uncompressed first compression spring 1580SB by first and second foot 1444A and 1446A sliding back up respective ramps 1552RR and 1552LR which then allows clips 1562A and 1564A to jump to the next slanted surface 1600-USL and 1600-RSL of the next tooth 1600-U and 1600-L.

This process continues as the operating pushbutton 1410 is pressed until the multi-section shaft 1570 is completely extended and the second compression spring 1580SR is completely compressed.

To retract the multi-section shaft back to its original or starting point, it is necessary to disengage the ratchet teeth 1600-U and 1600-L from the downwardly extending ratch tooth engagement clip 1562A and upwardly extending ratchet tooth engagement clip 1564A. Surrounding the exterior surface 1022 of the exterior wall 1020 of the dispensing pen 1000 at a location between the slide member 1570 and the upper shaft holder 1562-U and lower shaft holder 1564-L is a rotational switch 1700. Referring to FIGS. 2 and 3, the rotational switch 1700 is connected to a locking element 1710 attached to a cylindrical locking member 1720 physically attached to the multi-section shaft 1570. When the rotational switch 1700 is rotated, the locking element 1710 and cylindrical locking member 1720 also rotate, thereby causing the multi-section shaft 1570 to rotate until clips 1562A and 1564A are disengaged from the ratchet teeth 1600-U and 1600-L. Upon such disengagement, second compression spring 1580SR retracts the multi-section shaft 1070 back to its starting position. The rotational switch 1700 is rotated in the opposite direction back to its original position, the locking element 1710 and cylindrical locking member 1720 are also rotated back to their original position, thereby causing the multi-section shaft 1570 to rotate back its original position until clips 1562A and 1564A are re-engaged with the ratchet teeth 1600-U and 1600-L to begin the starting position.

Figure 6:
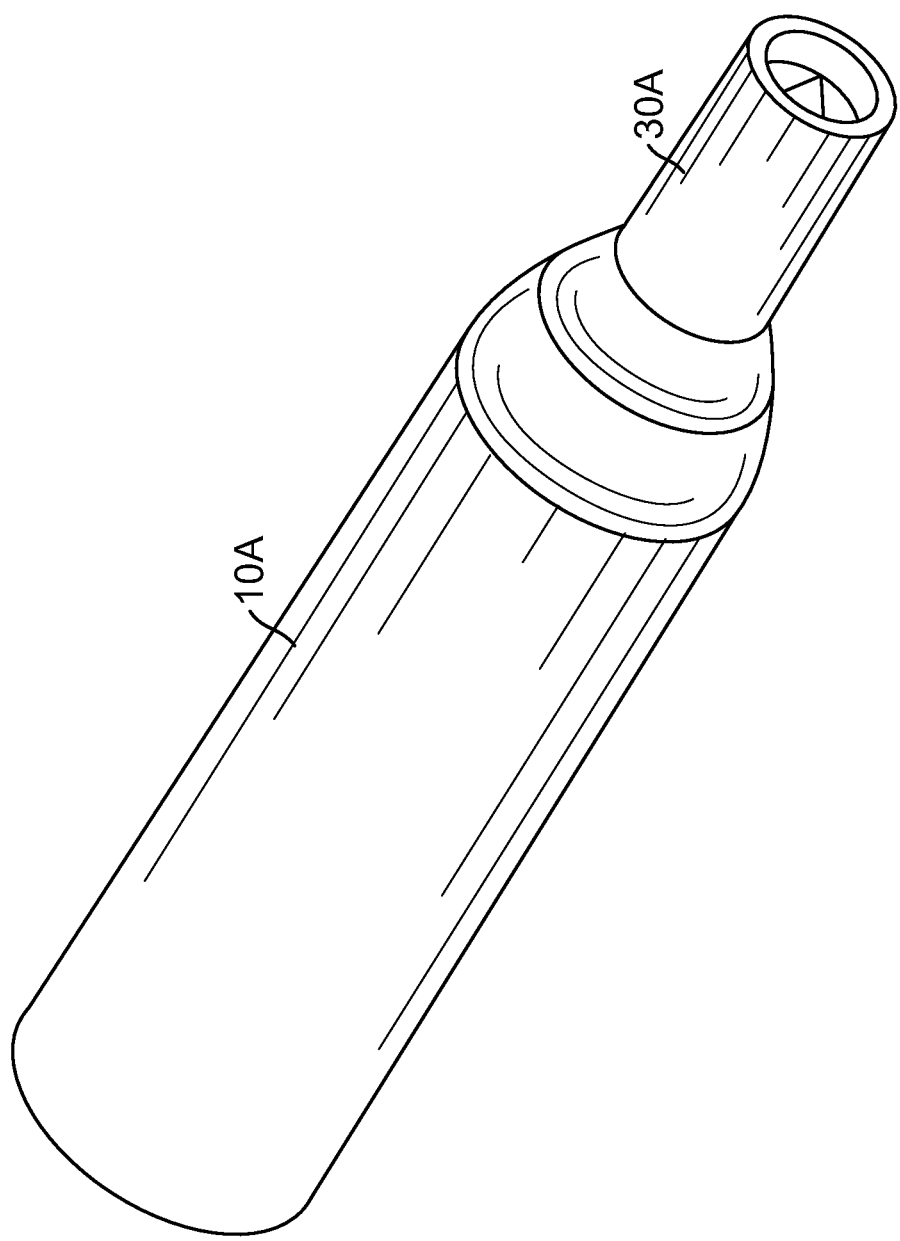
FIG. 6 is a top perspective view of the unidose single use cartridge which contains a compound as defined above including compound selected from the group consisting of a tooth whitening compound, a dental bonding and filling compound, and an adhesive compound in a sealed condition with the cap threadedly retained onto the single use cartridge, and which cartridge is disposed of and replaced with a new single use cartridge for subsequent application of a compound.
Figure 7:
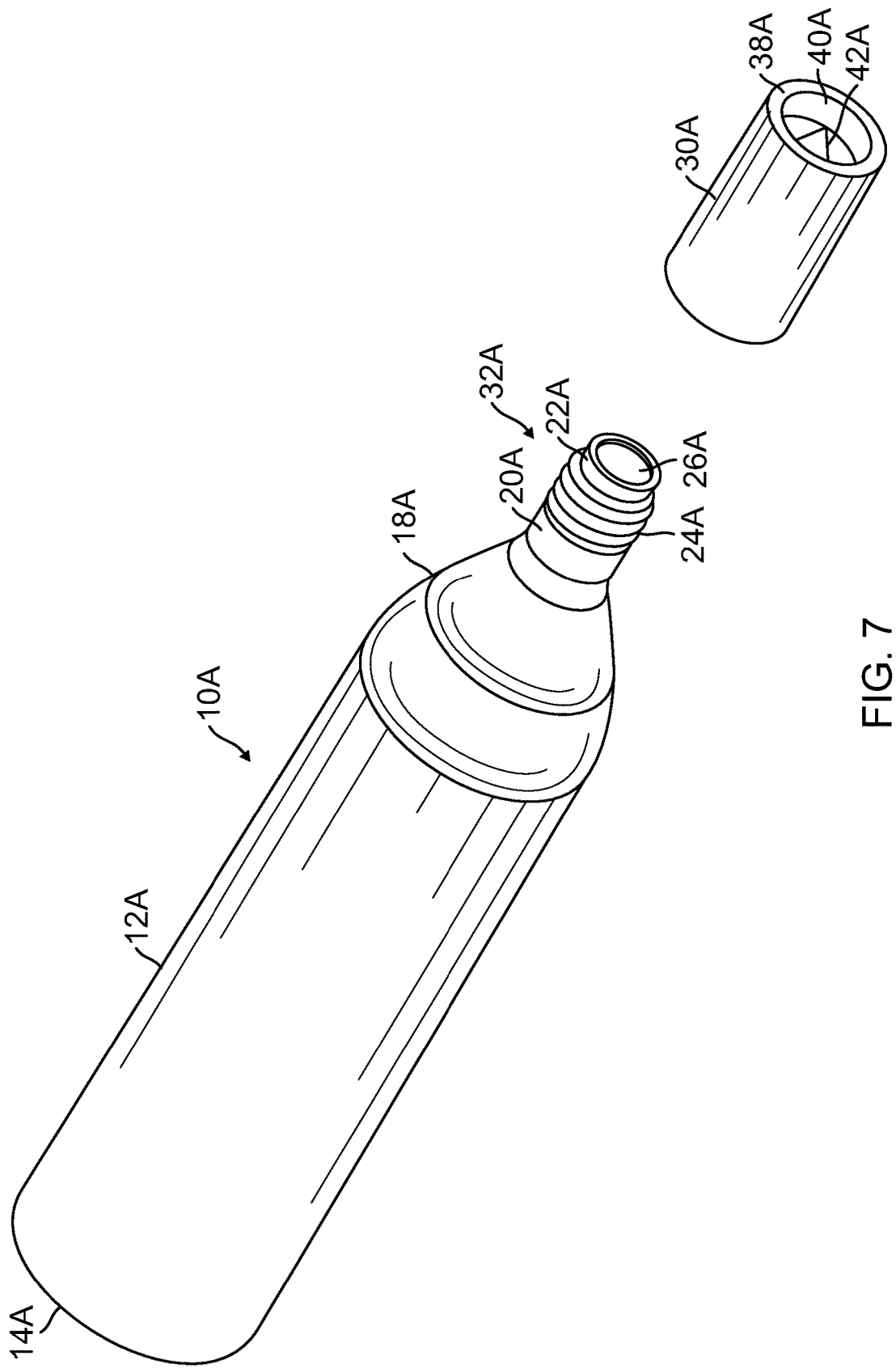
FIG. 7 is an exploded view showing the same capsule illustrated in FIG. 6 but with the sealing cap removed, the single use capsule or cartridge (the term capsule or cartridge are used interchangeably) having an exterior surface which is generally cylindrical in shape and a rear surface which is generally flat with an opening, a front surface which is generally frustum shaped extending from the body of the cylinder to a nozzle having a cylindrical surface extending from the frustum and extending to a dispensing nozzle tip having threads on the exterior surface and a frangible seal on the front end of the tip, also illustrating the threaded cap which is cylindrical and a front end with an interior chamber having a piercing tooth.
Figure 8:
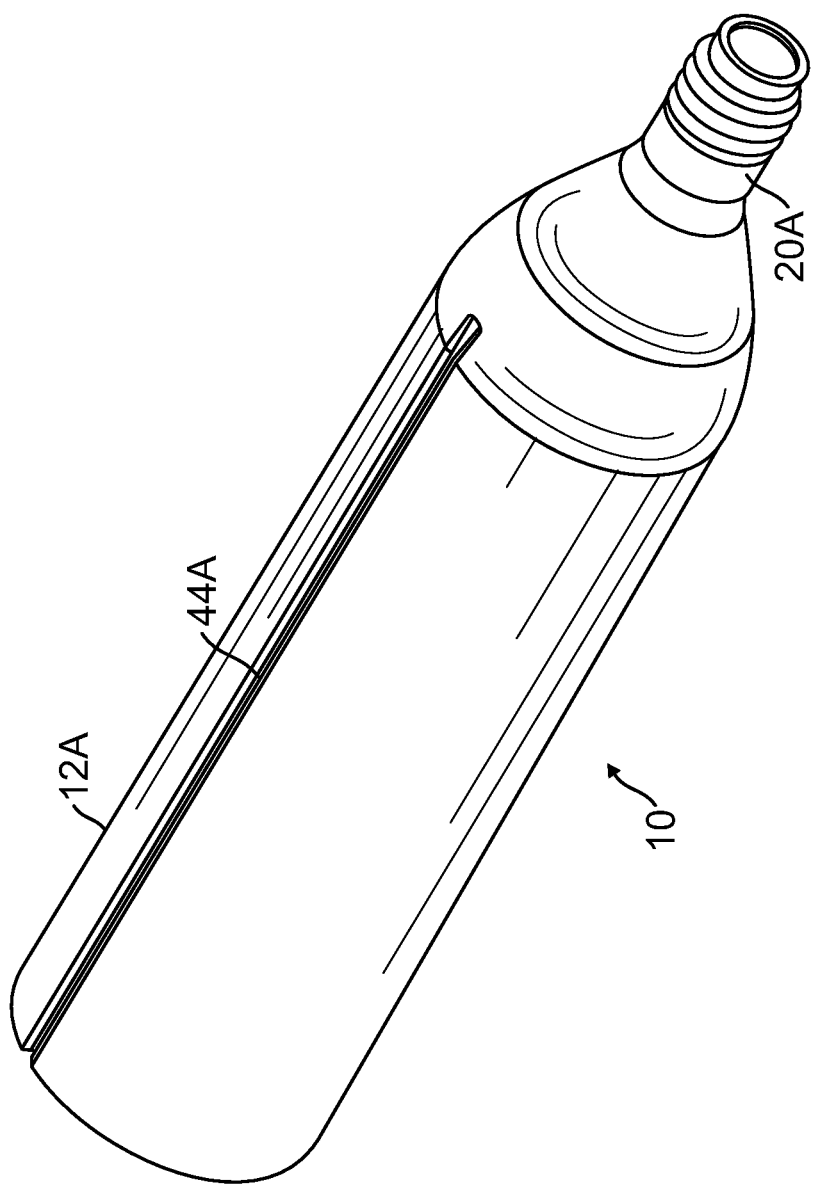
FIG. 8 is a bottom perspective view of the unidose single use cartridge with an anti-rotation slit in the bottom of exterior surface of the exterior wall of the tooth whitening retaining cartridge, the slit does not extend so deep that it goes into the interior chamber of the cartridge, the purpose of the anti-rotation slit is to be inserted into a mating member in the dispensing pen to prevent the cartridge from rotating once it is placed into the pen.

Referring to FIG. 6, there is illustrated an exterior perspective view of a cartridge or capsule 10A with a front cap 30A attached, which is used when the cartridge is inserted into an interior chamber within the dispensing pen 1000. The interior will vary as discussed above. For a single interior chamber cartridge, the letter "A" is used with a corresponding part. The letter "A" is not used when the interior of the cartridge 10 has a dual chamber. The exterior is the same for both. In FIGS. 6, 7 and 8, the letter "A" is used since the cross-sectional view of FIG. 9 illustrates a cartridge 10A with a single interior chamber.

Further referring to FIG. 7, there is illustrated an exploded exterior view of a single use capsule or cartridge 10A (the term capsule or cartridge are used interchangeably) with the cap 30 unscrewed. The single interior use cartridge 10A contains an exterior surface 12A which is generally cylindrical in shape and a rear surface 14A which is generally flat. The front surface 18A is generally frustum shaped extending from the body of the cylinder 10A to a nozzle 32A having a cylindrical surface 20A extending from the frustum 18A and extending to a dispensing nozzle tip 22A having threads 24A on the exterior surface and a frangible seal 26A on the front end of the tip 22A. The threaded cap 30A is cylindrical with a front end 38A with an interior chamber 40A having a piercing tooth 42A within the interior 40A which extends inwardly from the front end 38A of the sealing cap 30A. In use, after the cartridge 10A is placed in the dispensing pen 1000 as will be discussed, the front or tip 22A of the single use cartridge 10A extends through an opening in the dispensing pen and the threaded cap 30A which is previously unscrewed from the threads 24A of the capsule 30A before the capsule or cartridge 10A is inserted into the dispensing pen 1000, is then rotated 180 degrees so that the sharp tooth 42A penetrates the frangible seal 26A so that the tip 22A is opened and a selected compound 100A is dispensed from the interior 50A of the cartridge or capsule 10A.

Referring to FIG. 8, there is a illustrated bottom perspective view of the unidose single use cartridge 10A. The difference between the top view and the bottom view is that bottom view shows an anti-rotation slit 44A in the bottom of exterior surface 12A. The slit 44A does not extend so deep that it goes into the interior chamber as will be discussed. The purpose of the anti-rotation slit 44A is to be inserted into a mating member in the pen to prevent the cartridge 10A from rotating once it is placed into the interior chamber of the dispensing pen 1000.

Figure 9:
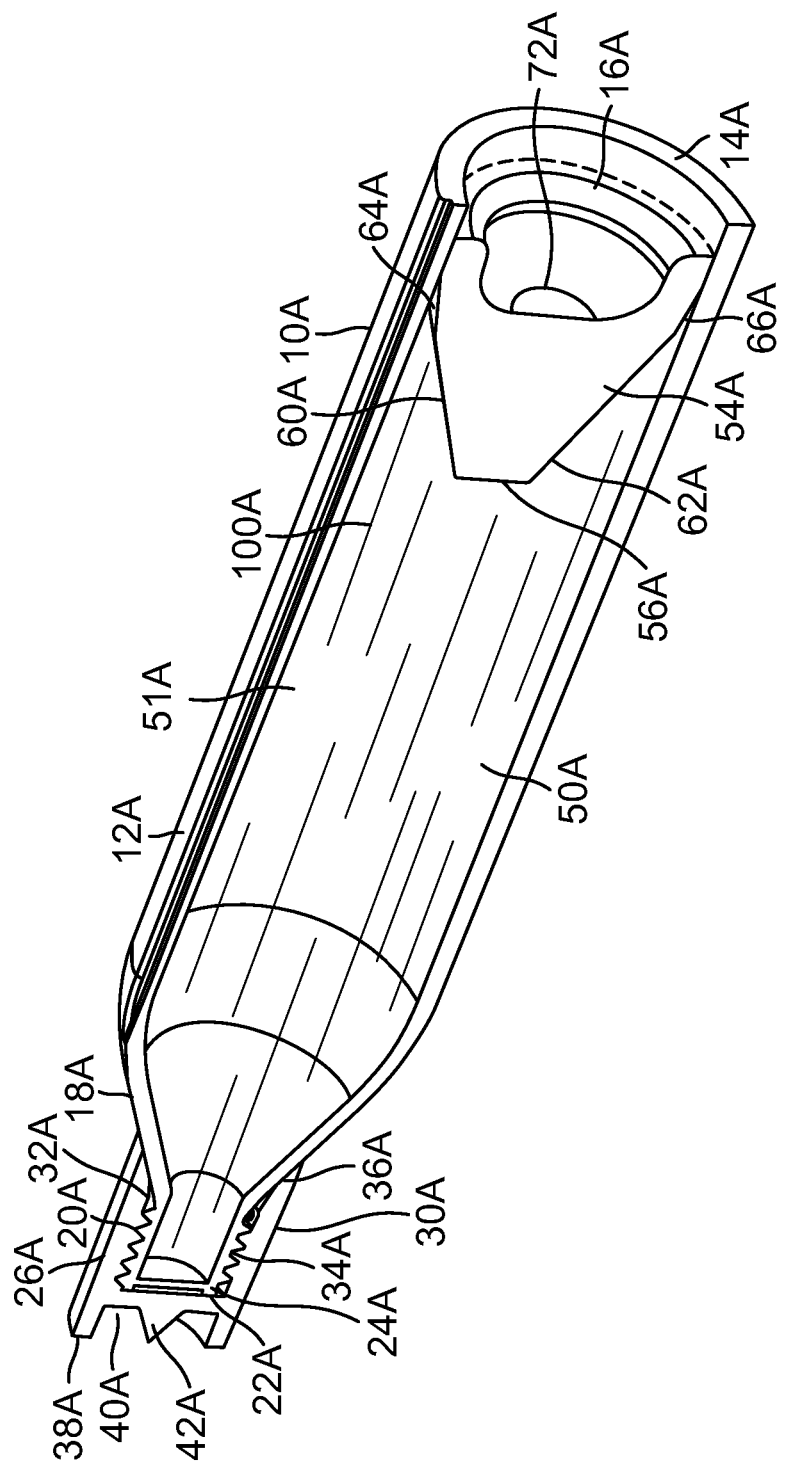
FIG. 9 is a side cross-sectional view of a first embodiment of the unidose single use cartridge illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston.

Referring to FIG. 9, there is illustrated a side cross-sectional view of a first embodiment of the unidose single use cartridge with sealing cap affixed, illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston. The cartridge 10A has a single interior chamber 50A with a single compound 100A retained in the interior chamber 50A. A rear plunger 54A having an interior face 56A is used to push the compound 100A in the interior chamber 50A forward and out of the cartridge 10A. The rear plunger 54A has a pair of opposed rear angular sides 60A and 62A extending from opposite ends of the interior face 56A and respectively ending in rear sidewalls 64A and 66A forming a seal against the interior sidewall 51A of the cartridge 10A, the interior of each rear sidewall 64A and 66A of the plunger 54A forming the sidewalls of a pocket 72A to receive the pushing piston from the retaining pen.

Figure 10:
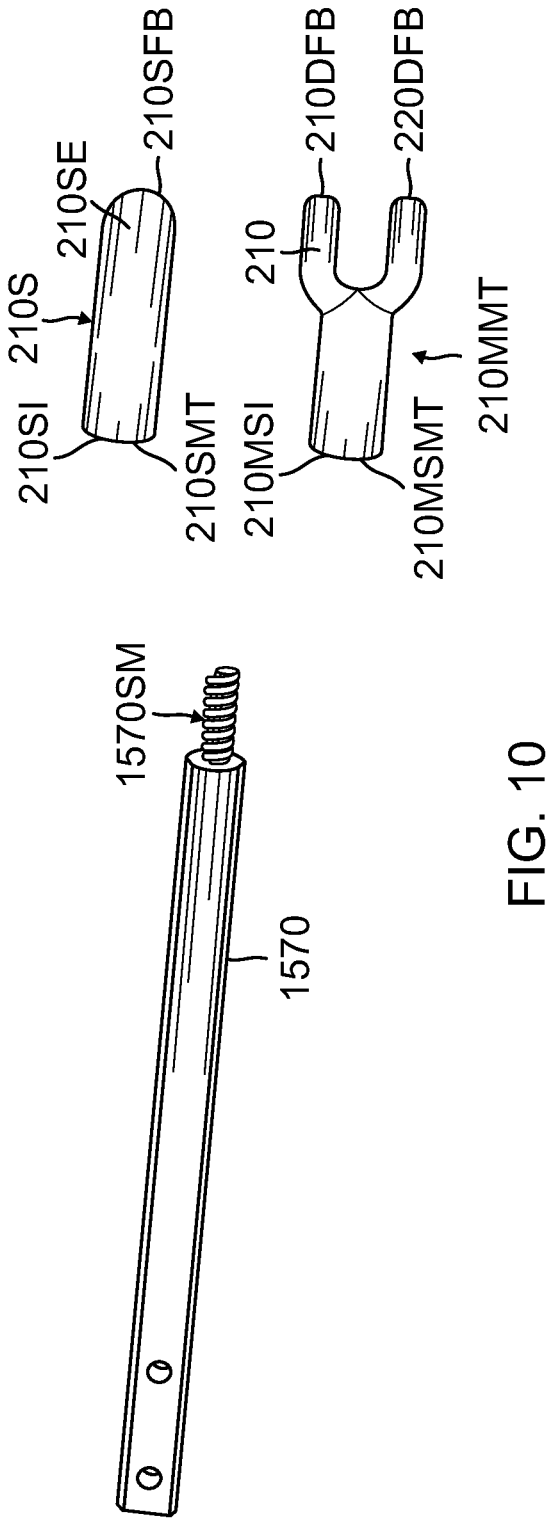
FIG. 10 is an exploded view illustrating the front of the multi-sectional shaft and a single piston and a dual piston.

Further referring to FIG. 9, the single use capsule or cartridge (the term capsule or cartridge are used interchangeably) with the single interior chamber 51A contains an exterior surface 12A which is generally cylindrical in shape and a rear surface 14A which is generally flat with an opening 16A through which a pushing piston 210S is inserted into pocket 72A, a front surface 18A which is generally frustum shaped extending from the body of the cylinder 10A to a nozzle 32A having a cylindrical surface 20A extending from the frustum 18A and extending to a dispensing nozzle tip 22A having threads 24A on the exterior surface and a frangible seal 26A on the front end of the tip 22A. A threaded cap 30A is cylindrical with an interior surface 32A with threads 34A adjacent the rear 36A of the sealing cap 30A and a front end 38A with an interior chamber 40A having a piercing tooth 42A within the interior 40A which extends inwardly from the front end 38A of the sealing cap 30A. In use, after the cartridge 10A is placed in the dispensing pen 1000 as will be discussed, the front or tip 22A of the single use cartridge 10A extends through an opening in the dispensing pen and the threaded cap 30A which is previously unscrewed from the threads 24A of the capsule 30A before the capsule or cartridge 10A is inserted into the dispensing pen 1000, and is then rotated 180 degrees so that the sharp tooth 42A penetrates the frangible seal 26A so that the tip 22A is opened and a selected compound 100A is dispensed from the interior 50A of the cartridge or capsule 10A Referring to FIG. 10, there is illustrated the two types of pushing pistons attached to the front of the multi-sectional shaft 1570 described in detailed when discussing FIGS. 1 through 5. The front 1570F of the multi-sectional shaft 1570 has a first mating member 1570SM which in an illustrative embodiment has male threads. There is a single piston 210S with a shaft second mating portion. 210SMT. For the illustrative embodiment where the first mating member 1570SM of the multi-sectional shaft 1570 has male threads, the shaft second mating portion 210SMT has mating female threads within the single piston 210S. In an embodiment, the single pushing piston 210S has a cylindrical exterior with a rounded bullet shaped front 210SE which is inserted into pocket 72A in the interior of single chamber cartridge 10A. The single pushing piston 210S has a partially hollow interior which would have the female mating threads. For a cartridge 10 having a dual chamber, the pushing piston 210 has a mating section 210MMT which branches into a first piston 210 and a spaced apart second piston 220. For the illustrative embodiment where the first mating member 1570SM of the multi-sectional shaft 1570 has male threads, the mating section 210MMT shaft second mating portion 210SMT has a partially hollow interior which would have mating female threads within its interior 210MSI. In an embodiment, the mating section 210MMT has a cylindrical exterior which branches into first piston 210 having a bullet shaped front 210DFB and a second piston 220 with a bullet shaped front 220DFB which are respectively inserted in pushing plunger pockets as will be described.

FIG. 1 illustrates a cross-sectional view where a pushing piston is placed onto the front end 1570F of the multi-sectioned shaft 1570. As illustrated in FIG. 1, in one variation, the single use cartridge is placed within an opening adjacent to front of the dispensing pen with the threaded nozzle extending through the opening in the front of the dispensing pen 1000. For the single chamber cartridge 10A illustrated in FIG. 7, the single piston mating section 210SMT is affixed to the front 1570F of the multi-section shaft 1570 and the single pushing piston 210S is guided into rear pocket 72A. For the dual chamber cartridge 10 illustrated in FIG. 8, the mating section 210MMT is affixed to the front 1070S of the multi-section shaft and a respective one of the dual pushing pistons 210 and 220 is guided into a respective pocket 68 and 70.

Figure 11:
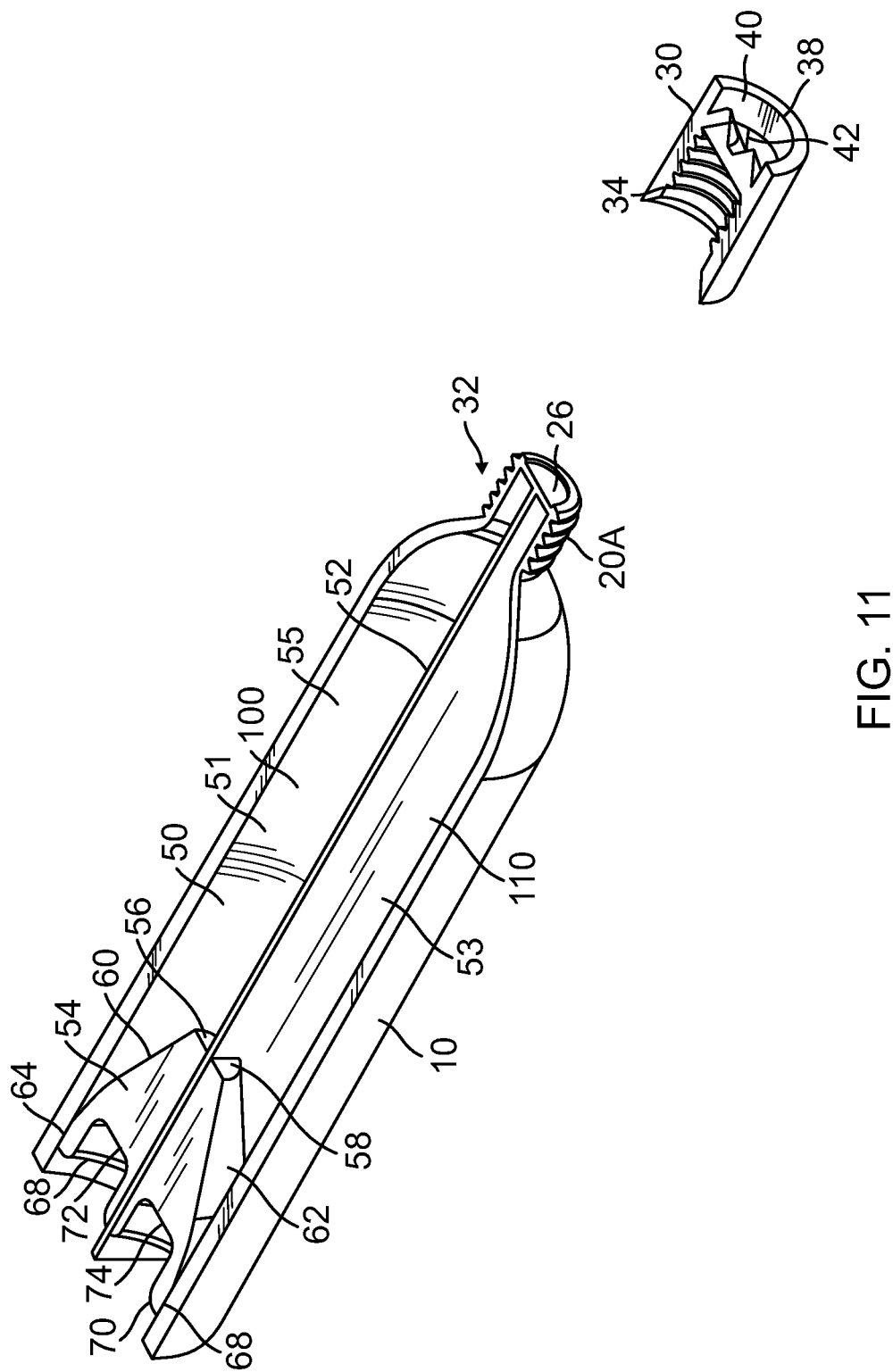
FIG. 11 is a top cutaway view of a second embodiment of the unidose single use cartridge having a divided interior chamber which retains two separate compounds which are separated from each other while in the cartridge by a dividing wall, and a rear plunger having opposing interior faces to push a compound in a respective portion of the interior of the cartridge forward and out of the cartridge, and a pair of opposed angular sidewalls ending in rear wall sidewalls forming a seal against the interior sidewall of the cartridge, each rear end of the plunger having a pocket to receive a respective pushing piston from the dispensing pen.

Referring to FIG. 11, the alternative cartridge 10 with a dual chamber interior is illustrated in a top cutaway view of the second embodiment of the unidose single use cartridge 10 containing the divided interior chamber 50 which retains two separate compounds 100 and 110 which are separated from each other while in the cartridge by a dividing wall 52, and a rear plunger 54 having opposing interior faces 56 and 58 to push a compound 100 or 110 in a respective portion of the interior 50 of the cartridge forward and out of the cartridge 10, and a pair of opposed angular sidewalls 60 and 62 ending in rear wall sidewalls 64 and 66 forming a seal against the interior sidewall 51 of the cartridge, each rear end 68 and 70 of the plunger 54 having a pocket 72 and 74 to receive a respective pushing piston from the dispensing pen 1000. Referring to FIG. 8, it can be seen that the chamber 50 is divided into two equal chambers 53 and 55 which contain different compounds which cannot come in contact with each other because the dividing wall 52 extends for the entire diameter "D1" and Length "L1" of the interior chamber 50 of the cartridge 10. For dual compounds where less is need of one of the two compounds, the dividing wall 52 is thicker on one side to reduce the volume of compound in the smaller chamber, the design of the plunger is modified to accommodate the revised sidewall 52. Figure also shows the frustum shaped front and threaded nozzle and threaded cap with a piercing tip. This portion of the cartridge 10 having a frustum shaped front leading to a threaded nozzle 32 with threads 20 and a frangible seal 26 and threaded cap 30 with interior mating threads 34, a piercing element 42 in an interior 40 of front 38 of cap 30.

Figure 12:
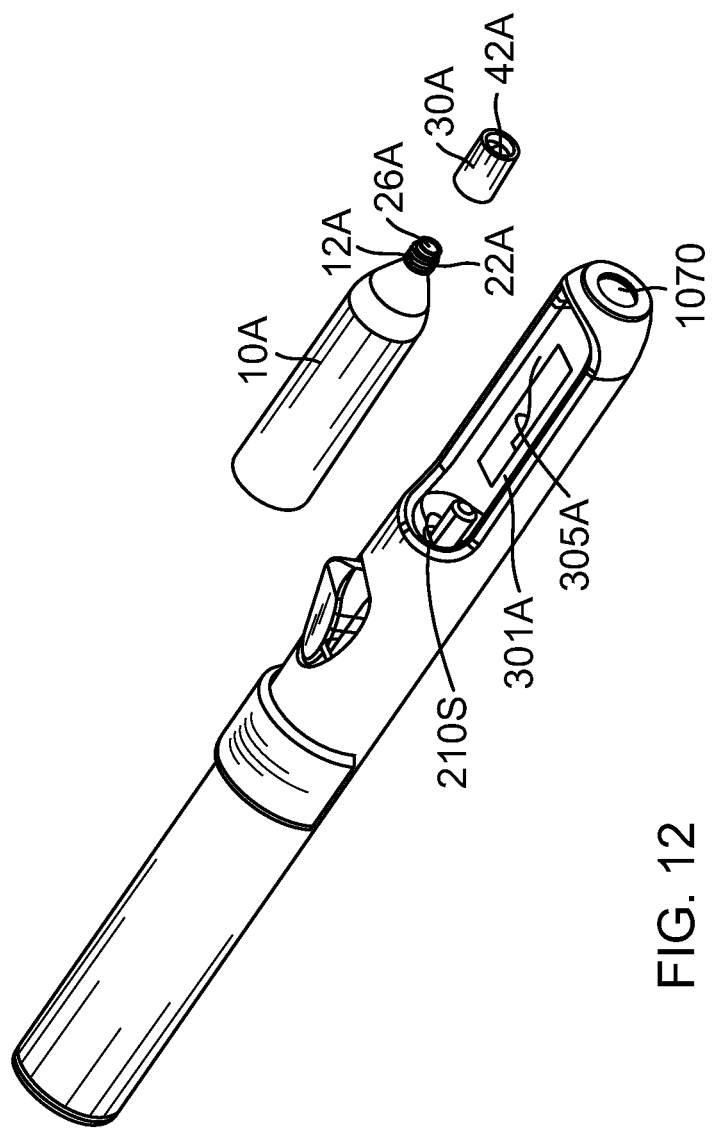
FIG. 12 is an exploded view illustrating a top right perspective view of the unidose dispensing pen with a single piston affixed to the new and novel ratchet operating mechanism illustrated in FIG. 1 within the dispensing pen, and a single chamber cartridge before it is inserted into a chamber adjacent the front of and within the dispensing pen and also illustrating a cartridge anti-rotation member within the chamber.

Referring to FIG. 12, there is illustrated a top right side view of the present invention unidose dispensing pen with the new and novel ratchet dispensing mechanism 1400 illustrated in FIGS. 1 through 5 retained within the dispensing pen 1000 including illustrating the operating pushbutton 1410, the ratchet disengagement switch 1700, the open chamber 301A with an anti-rotation member 305A and the opening 1090. The cartridge 10A with cap 30A removed is inserted into chamber 301A with anti-rotation member 305A engaging anti-rotation slit 44 in the bottom surface of cartridge 10A with threads 22A protruding through opening 1090. Single pushing piston 210S is also illustrated.

Figure 13:
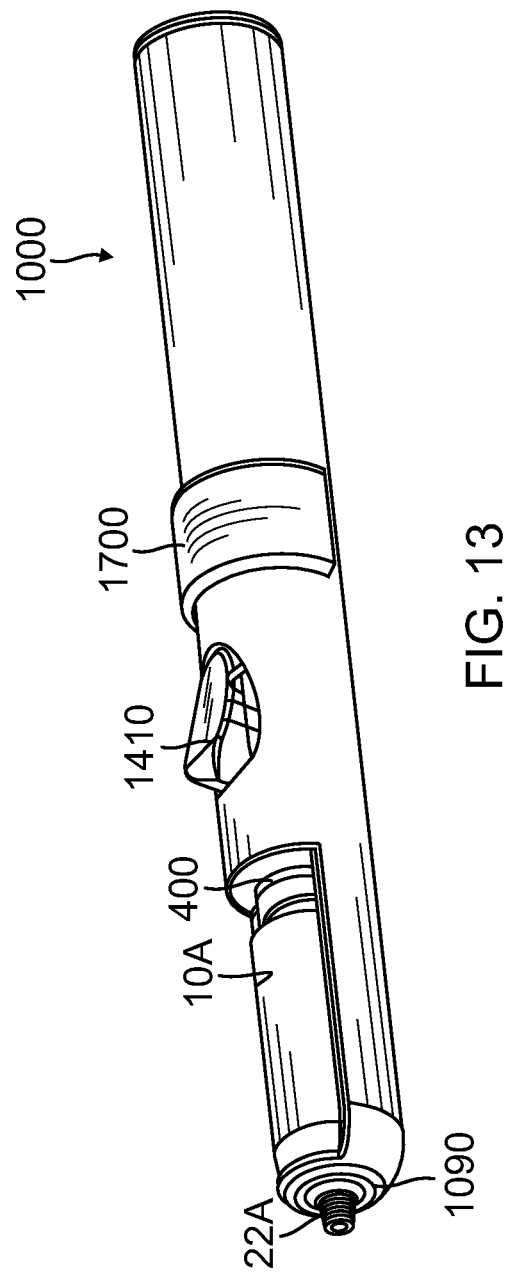
FIG. 13 is a top right side perspective view of the dispensing pen of the present invention as illustrated in FIG. 12, with the cartridge within the dispensing pen having the new and novel ratchet mechanism of the present invention as illustrated in FIGS. 1-5, with the single use cartridge retained within the interior chamber of the dispensing pen with the front portion of the top removed and the threaded nozzle protruding through the front opening of the dispensing pen.

FIG. 13 is a top left side perspective view of the present invention unidose dispensing pen 1000 with the new and novel mechanical ratchet dispensing mechanism 1400 illustrated in FIGS. 1 to 5 retained within the dispensing pen 1000 including illustrating the operating pushbutton 1410, the ratchet disengagement rotational switch 1700, a visible portion of an exterior of a pushing piston 210S and a single use cartridge 10A within the dispensing pen 1000.

It will be appreciated that the dual chamber cartridge 10 is inserted the same way. As illustrated in FIG. 1, in one variation, the single use cartridge 10A is placed within an opening 301A adjacent to front 1080 of the dispensing pen 1000 with the threaded nozzle 20A extending through the opening 1090 in the front 1080 of the dispensing pen 1000. For the single chamber cartridge 10A illustrated in FIG. 9, the single piston mating section 210SMT is affixed to the front 1570F of the multi-section shaft 1570 and the single pushing piston 210S is guided into rear pocket 72A. For the dual chamber cartridge 10 illustrated in FIG. 11, the mating section 210MMT is affixed to the front 1570F of the multi-section shaft 1570 and a respective one of the dual pushing pistons 210 and 220 is guided into a respective pocket 68 and 70.

In operation, the multi-sectioned shaft 1570 in incrementally moved forward by the present invention operating ratchet mechanism illustrated in FIGS. 1 to 5 and discussed above. For the single chamber cartridge 10A, pushing piston 210A is used to engage a pocket 72A of the single-pocket plunger 54A used with a single chamber cartridge and the ratchet mechanism of the present invention moves the pushing piston 210S in the forward direction to push the plunger 54A forwardly to dispense a selected compound 100 out of the cartridge through nozzle 10A For the dual chamber cartridge 10, pushing pistons 210 and 220 are respectively used to engage a respective pocket 72 and 74 of the two-pocket plunger 54 used with the dual chamber cartridge and the ratchet mechanism of the present invention moves the two pushing pistons 210 and 220 in the forward direction to push the plunger 54 forwardly to dispense a selected compound 100 and 110 out of the cartridge through nozzle 10. For the single chamber cartridge 10A, the ratchet mechanism incrementally moves the move the pushing piston 210S forwardly to move the plunger 54A forwardly to push the compound 100A out of the cartridge 10S through nozzle 30S. If the volume of he two compounds is different, the dividing wall 52 is thicker on one side to reduce the volume of compound in the smaller chamber, the design of the plunger is modified to accommodate the revised sidewall 52.

Figure 17:
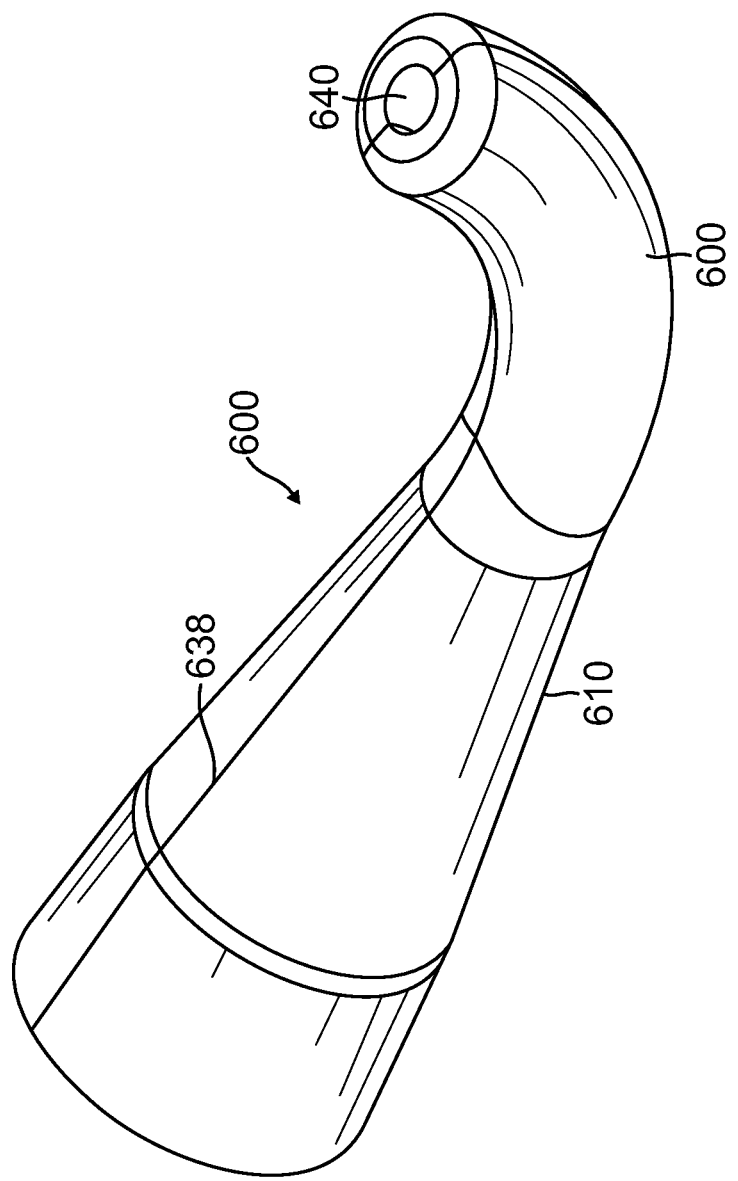
FIG. 17 is a perspective view of a bent horn tip dispensing nozzle used with a single chamber cartridge or used with a mixing tip dual chamber cartridge.

FIG. 17 are the same as in FIGS. 5, 6, 7 and 8 with an "S" at the end of each number.

Except for combining two compounds in a mixing nozzle, the operation after the compound is pushed out of the cartridge is the same.

Referring to FIG. 1, there is illustrated a top perspective view of the unidose single use cartridge 10 which contains a compound as defined above including compound selected from the group consisting of a tooth whitening compound, a dental bonding and filling compound, and an adhesive compound in a sealed condition with the cap 30 threadedly retained onto the single use cartridge 10, and which cartridge is disposed of and replaced with a new single use cartridge for subsequent application of a compound.

Figure 14:
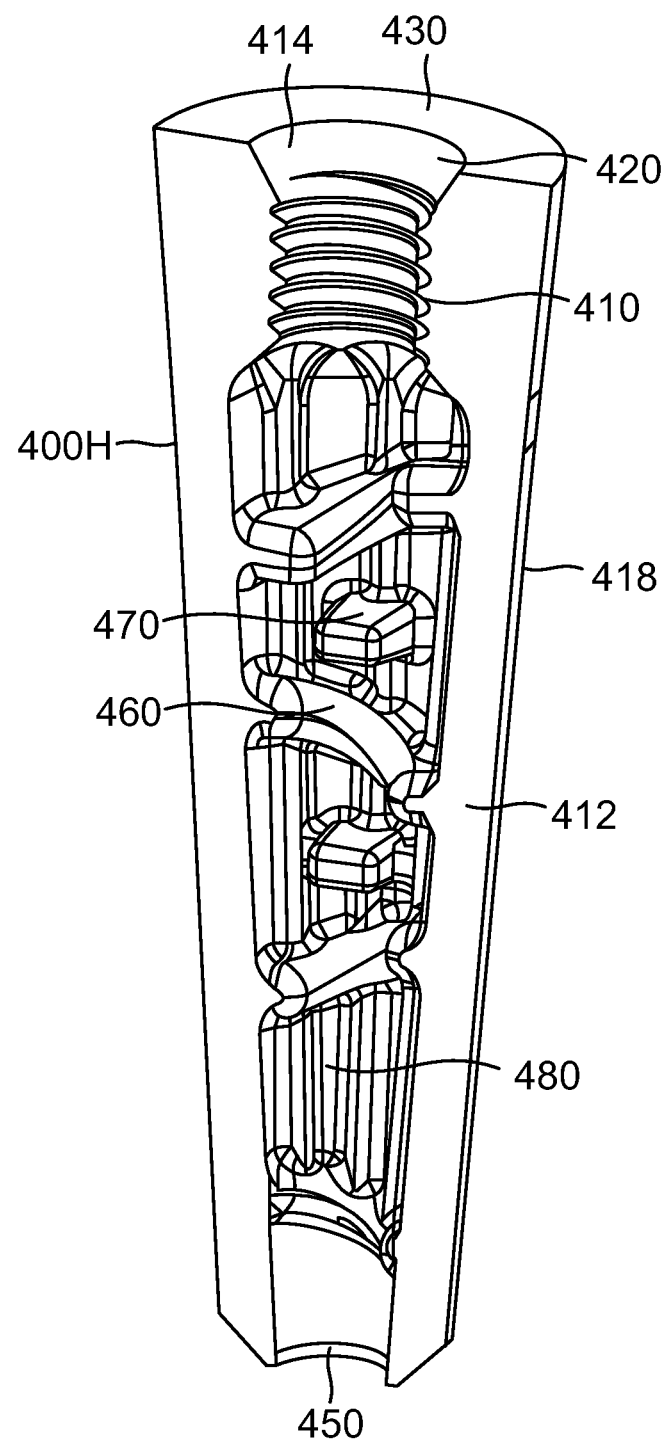
FIG. 14 is a longitudinal cross-sectional view of the mixing nozzle of the present invention used with a cartridge having a divided interior housing two separate compounds.
Figure 14A:
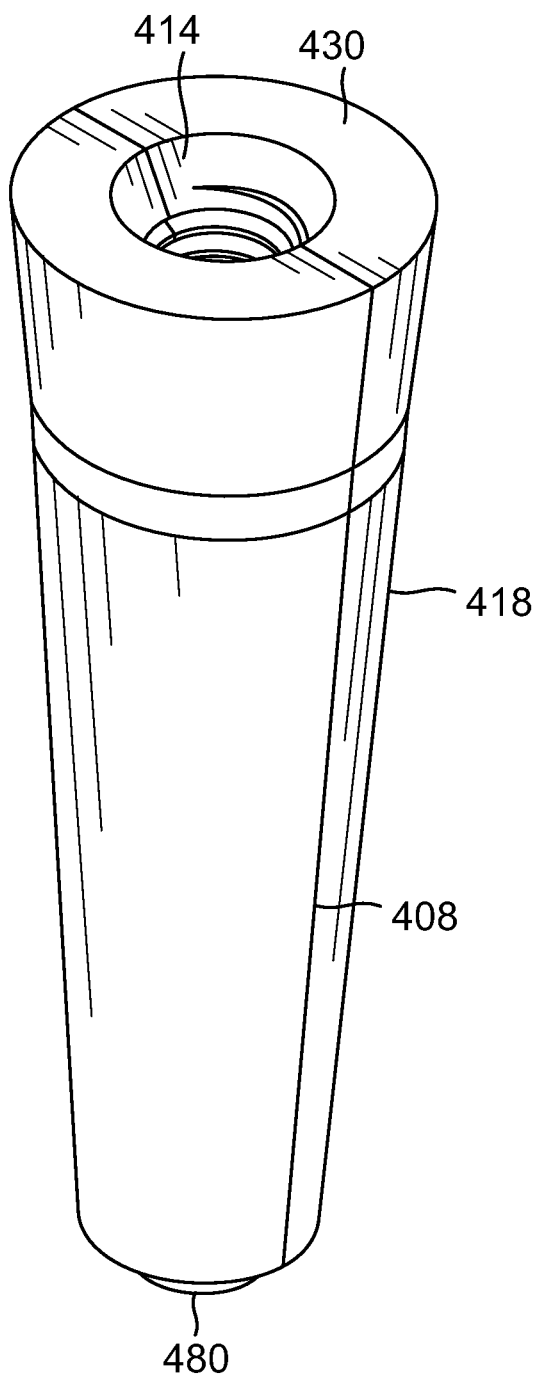
FIG. 14A is perspective view of the entire mixing nozzle including the two halves as illustrated in FIG. 14 sonic welded together at their respective mating surfaces at a location illustrated along a seam line to form an entire mixing tip.

Referring to FIG. 14, there is illustrated a cross-sectional view of one half 400H of the mixing nozzle 400 which is used with a dual chamber cartridge. The mixing nozzle 400 has internal threads 410 on its internal surface 420 adjacent its rear end 430 and on nuts external surface 418 external threads 440 adjacent its front end 450 and contains a multiplicity of semi-closed shelves 460 and also straight shelves 470 so that as the compounds 100 and 110 are driven through the mixing nozzle 400, the angular shelves 460 and the straight shelves 470 cause the compounds 100 and 110 to mix together and go through a series of angular shelves 460 and straight shelves 470 to make sure that the compound is fully mixed when it gets to the opening 480 of the mixing chamber 400. A rear opening 414 permits the compounds 100 and 110 to enter the mixing tip 400 after it is screwed onto the threads 24 of tip 26 of capsule 10. FIG. 9 illustrates one half of the mixing nozzle. The opposite half is a mirror image of half 400H. The two halves of sonic welded together along their longitudinal interior faces 412 to form a complete mixing nozzle 400 illustrated in FIG. 14A. Referring to FIG. 14a, there an exterior view of the mixing nozzle with a seam line 408 illustrates the location of the sonic weld.

A key innovation of the present invention mixing nozzle 400 is that it is comprised of internal built in shelves which thoroughly mix the compound portions as they are forced through the mixing nozzle. This is a major improvement over the prior art where an insert is placed into a chamber and compounds mixed through the insert which leads to less mixing and much more inefficiency in the mixing.

Figure 15:
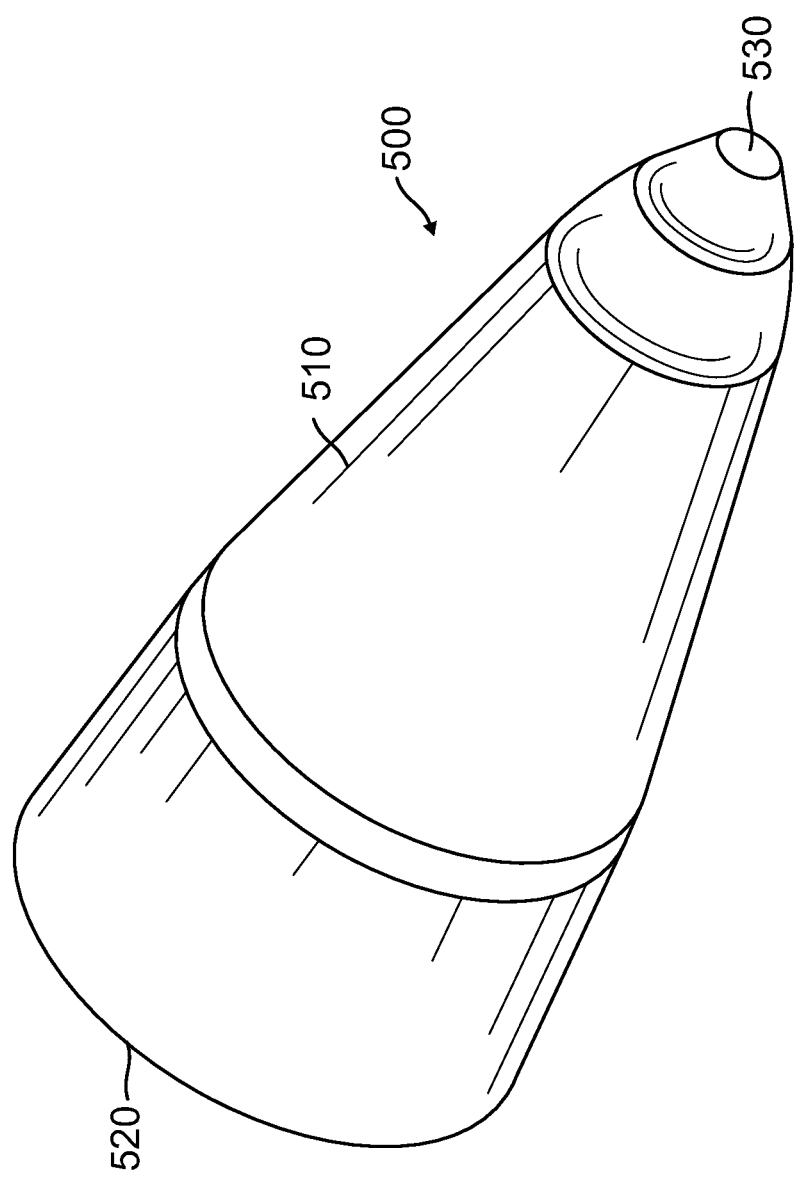
FIG. 15 is a perspective view of a straight dispensing nozzle used with a single chamber cartridge or used with a mixing tip and a dual chamber cartridge.
Figure 16:
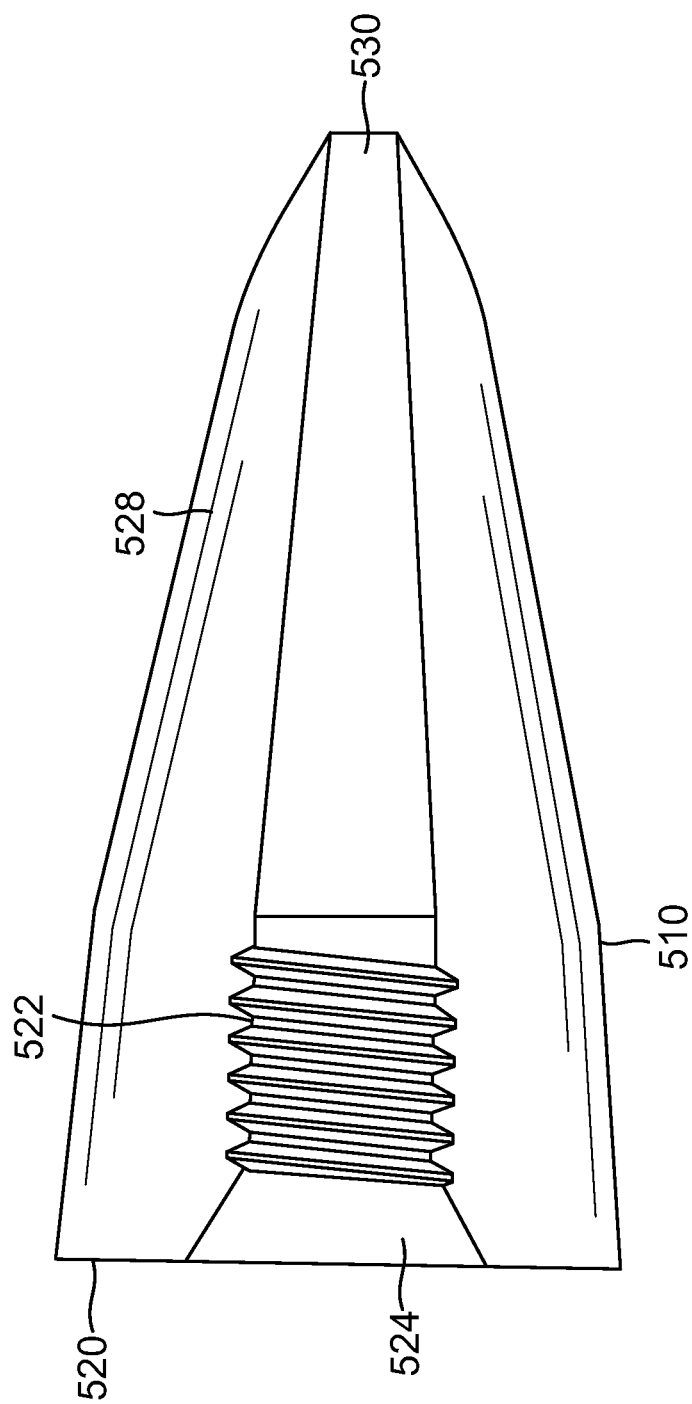
FIG. 16 is a cross-sectional view of the straight dispensing nozzle illustrated in FIG. 15.

Referring to FIGS. 15 and 16, there is illustrated a straight applicator 500 which contains an exterior surface 510 and an interior chamber 528 which has a widened end 520 with interior threads 522 surrounding a rear opening 524 that either thread around the end of the mixing tip or thread around the threaded end of the compound capsule and a front opening 530 through which the compound is dispensed. The compound enters through rear opening 524 and exits through front opening 530.

Figure 18:
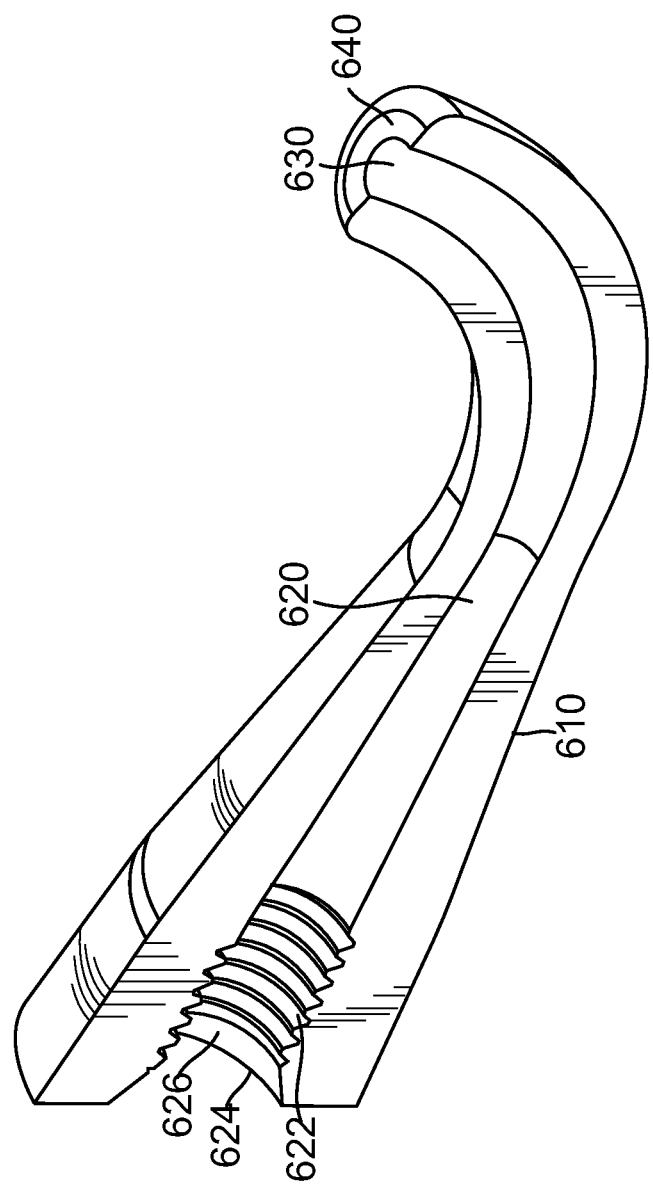
FIG. 18 is a cross-sectional view of the bent horn tip dispensing nozzle used with a single chamber cartridge or use with a mixing top dual chamber cartridge.

In an alternative embodiment illustrated in FIGS. 17 and 18, the applicator is a horn-shaped applicator 600 which has an exterior wall 610 and an interior chamber 620 which has a rear opening 624 and a rear interior wall 526 having threads 622 which can be threaded onto the end of the mixing tip or threaded onto the end of the tooth whitening compound cartridge and also has an opening 630 in front end 640 which is bent at an angle so that the tooth whitening compound can be applied to rear surface or to teeth near the back of the patient's mouth, the dental bonding compound can be applied to rear teeth fillings and the adhesive compound can be applied at a rear area of objects to be bonded together. The selected compounds enter from rear opening 624 and exits through front opening 640.

Referring to FIG. 12 (before the cartridge 10 or 10A is inserted into the pen 1000) and FIG. 13 (after the cartridge 10 or 10A is inserted into the pen 1000) there is illustrated an exploded view showing how the mixing pen operates. The cartridge 10A containing the compound 100 is inserted into chamber 301A near the front of the dispensing pen 1000 where the pocket 72A of the plunger 54A is retained against the single piston 210S and the front tip 12A of the cartridge 10A extends out of the opening 1090 in the pen 1000. The anti-rotation slit 44 on the cartridge is placed into the anti-rotation longitudinal stop shelf 305A in chamber 301A so the cartridge 10A will not rotate once inside the dispensing pen 1000. The sealing cap 30A is shown removed from the cartridge 10A. After the cartridge is inserted into the dispensing pen 1000, the cap 30A is used to penetrate the frangible seal 26A of the tip 22A of the cartridge 10A which extends out of the opening 1090 in the dispensing pen 1000 and thereafter either the straight applicator 500 or the horn-shaped applicator 600 is threaded onto the threads 22A of the cartridge 10A so that as the ratchet mechanism causes the piston 210S to move toward the front of the dispensing pen 1000, the piston 210S pushes on the back of the plunger 54A causing the plunger 54A to move the compound 100 out of the cartridge 10A into an applicator. For the dual chamber interior cartridge 10 containing the compounds 100 and 110 is inserted into chamber 301A near the front of the dispensing pen 1000 where the pockets 72 and 74 of the plunger 54 are retained against the dual pistons 210 and 220 and the front tip 12 of the cartridge 10 extends out of the opening 1090 in the pen 1000. The anti-rotation slit 44 on the cartridge is placed into the anti-rotation longitudinal stop shelf 305A in chamber 301A so the cartridge 10 will not rotate once inside the dispensing pen 1000. The sealing cap 30 is shown removed from the cartridge 10. After the cartridge is inserted into the dispensing pen 1000, the cap 30 is used to penetrate the frangible seal 26 of the tip 22 of the cartridge 10 which extends out of the opening 1090 in the dispensing pen 1000 and thereafter the mixing tip 400 is threaded onto the cartridge 10e and either the straight applicator 500 or the horn-shaped applicator 600 is threaded onto the mixing tip 400 so that as the ratchet mechanism causes the pistons 210 and 220 to move toward the front of the dispensing pen 1000, the pistons 210 and 220 push on the back of the plunger 54 causing the plunger 54 to move each compound 100 and 110 from each separate section of the cartridge 10 into the mixing tip 400 where the compounds 100 and 110 are mixed and then exit the mixing tip 400 into the applicator so that the mixed tooth whitening compound is either placed in a dental tray or placed on the patient's tooth.

Figure 19:
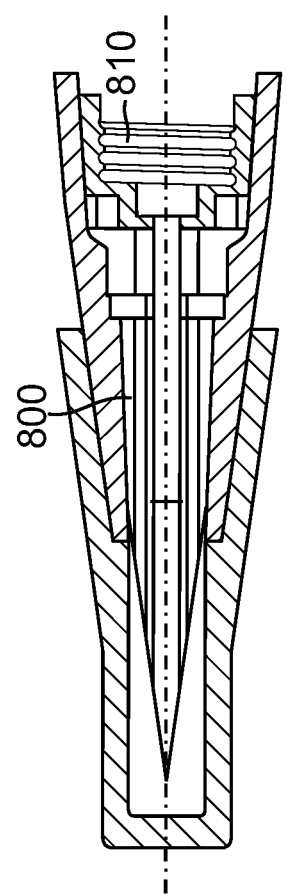
FIG. 19 is a cross-sectional view of an applicator brush.

Referring to FIG. 19 there is illustrated an applicator brush 800 which has interior mating threads which are threaded onto the exterior threaded nozzle of the single use cartridge from which compound is dispensed onto the brush or onto the mixing tip nozzle for the dual chamber cartridge.

Figure 20:
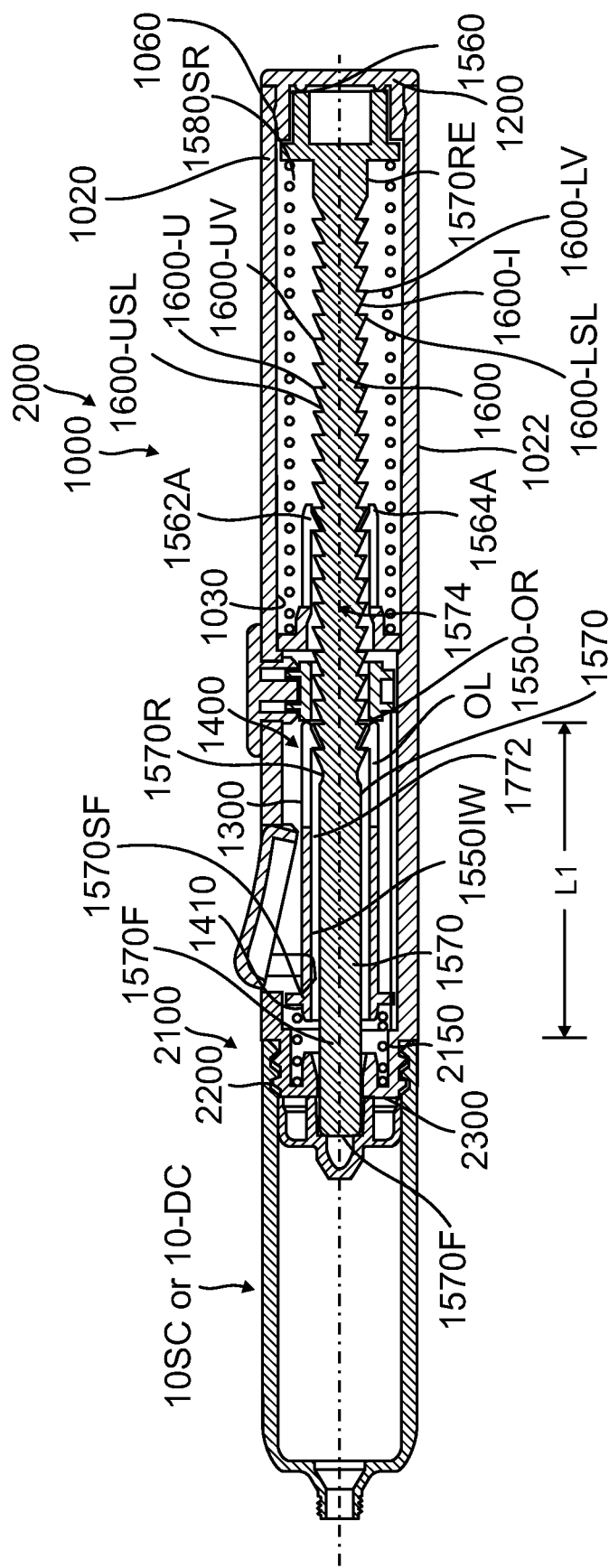
FIG. 20 is a cross-sectional view of the dispensing pen which retains the new and novel mechanical ratchet mechanism of the present invention, with a single use cartridge threaded onto the front of the cartridge, the single use cartridge being either a single chamber cartridge as previously described with a single pushing piston or a dual chamber cartridge with a dual piston as previously described, the applicators and mixing chamber, as required respectively threaded onto the threaded nozzle in the front of the cartridge.
Figure 21:
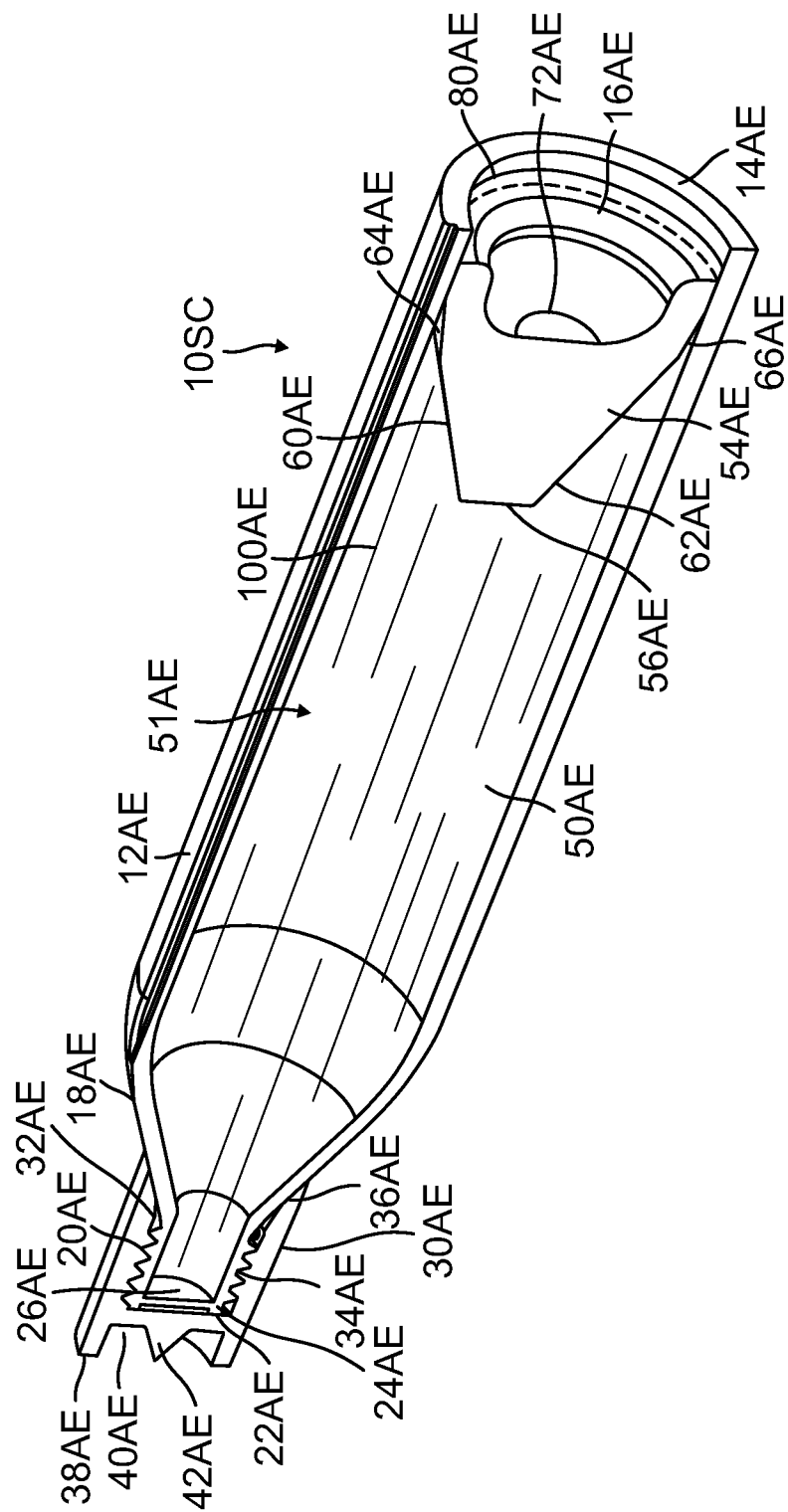
FIG. 21 is a side cross-sectional view of a first embodiment of the unidose single use cartridge illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston, where the single chamber cartridge is retained on the front of the dispensing pen.

In a variation of the cartridge location, referring to FIG. 20, there is a perspective view of the dispensing pen 2000 which for the interior operating ratchet mechanism 1570, functions the same as the previous dispensing pen 1000. The difference is that instead of having the reusable cartridge 10 or 10A within a chamber within the dispensing pen, the dispensing pen has a front section 2100 which has a threaded exterior surface 2150 having mating threads 2200 thereon. The multi sections movable shaft 1570 has its front end 1570F pushed forwardly of the section 2100 through an opening 2300 through which the multi section shaft protrudes. The variation of the reusable cartridge is the same as shown in FIGS. 9 and 11 but instead has internal threads thereon. Referring to FIG. 21, for the single use cartridge having a single chamber which will be described as 10-SC, the single use cartridge having a single interior chamber has interior threads 80AE which mate with the exterior threads 2200 at the front of the dispensing pen 2000. As a result, instead of being within the chamber, the single use cartridge with internal threads 80AE now is extending from the front of the cartridge. The operating mechanism is the same as before with the single piston 210S affixed to the front 1570F of multi-sectional shaft 1570 and moved forwardly in increments by the novel and unique operating ratchet mechanism of the present invention to move pocket 72AE of pushing plunger 54AE. The compound is moved through the exterior cartridge 10A-SC through its exterior nozzle 20AE which also has threads and then dispensed into any of the applicators or any identified in FIGS. 15 to 18. The remaining components are numbered similar to the numbers in FIG. 9 but are numbered with AE.

Figure 22:
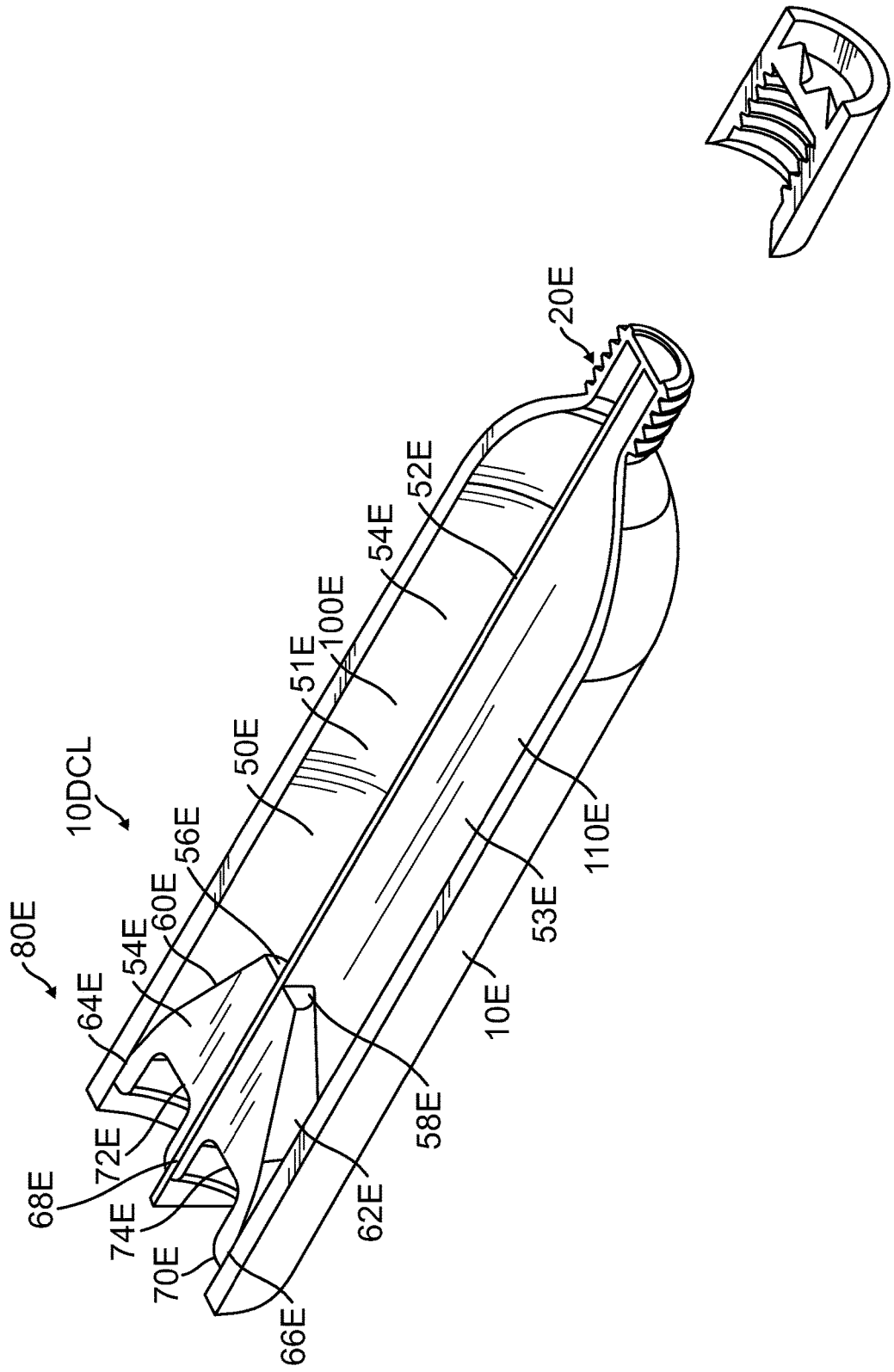
FIG. 22 is a top cutaway view of a second embodiment of the unidose single use cartridge having a divided interior chamber which retains two separate compounds which are separated from each other while in the cartridge by a dividing wall, and a rear plunger having opposing interior faces to push a compound in a respective portion of the interior of the cartridge forward and out of the cartridge, and a pair of opposed angular sidewalls ending in rear wall sidewalls forming a seal against the interior sidewall of the cartridge, each rear end of the plunger having a pocket to receive a respective pushing piston from the dispensing pen.

Alternatively, for a dual chamber cartridge, the mechanism described in FIG. 22 is applied to the front of the pen 2000 so that multi section movable shaft 1570 extends into a respective pocket of the dual chamber cartridge which since it is an exterior cartridge will be referred to as 10-DC. This exterior cartridge also has internal threads 80E which are threaded onto the mating threads 2100 of the second variation of the reusable pen so that the respective pistons 210 and 220 is moved into a respective pocket 72E and 74E of the exterior dual chamber reusable cartridge so that the dual compound is respectively pushed through the cartridge and out the exterior nozzle 20E and then into the mixing chamber which is threaded onto the exterior surface of the cartridge with the same process as previously discussed. The remaining components are numbered similar to FIG. 11 with "E" after each number.

The compound that is used with the present invention can be any multiplicity of compounds as previously discussed. The single use cartridge, whether it is retained within the dispensing pen or 10-SC which is exterior to the dispensing pen, can be any compound. If, by way of example, the compound 100 is a tooth whitening compound, then after being dispensed from the single use cartridge, the tooth whitening compound is placed in the dental tray where the tray is placed over the patient's teeth for a period of time or the tooth whitening compound is directly applied to the patient's teeth through a brush 800 as illustrated in FIG. 19. Alternatively, if it is a dual chamber single use cartridge 10, then two compounds 100 and 110 go through the chamber as tooth whitening compounds and then are combined together when they exit the nozzle 20E and go into the mixing chamber 400 where the two tooth whitening compounds are combined together in the mixing chamber 400 before they can be dispensed into a dental tray or other dental applicator.

Similarly, the compounds can be any type of products such as a glue, an adhesive, a powder, a gel, a cream, paint, cosmetics, lipstick, non-medicated cosmetics, medicated cosmetics, construction material compounds and virtually any other compound. If the compound does not need to be mixed with another compound, then a single use cartridge is used. If the compound needs to be mixed with another compound, then the dual chamber cartridge is used where they are respectively pushed through the dual chamber cartridge and then through the front nozzle and into the mixing nozzle where the two compounds are mixed together before they then can be applied to any one of the applicators or brushes set forth in FIGS. 15 to 18.

Figure 23:
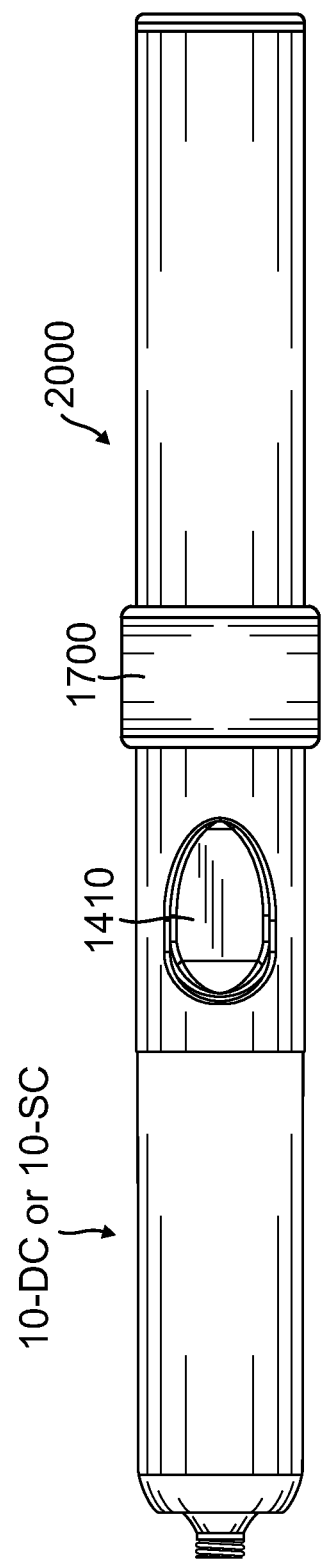
FIG. 23 is a top view of the present invention dispensing pen in the closed position.

Referring to FIG. 23, there is a perspective view of the revised dental dispensing pen 2000 illustrating an exterior cartridge 10-SC or 10-DC threaded onto the front of the dispensing pen 2000 where the ratchet removable switch 1700 and the pushbutton 1410 are illustrated. The operation of the mechanism is the same as before and the new and novel operating ratchet mechanism incrementally pushes a single piston or a dual piston through a respective pocket or dual receiving pocket in the single use chamber to push the compound through the chamber where it can be either sent to a mixing chamber for mixing or directly applied through an applicator. If it is first sent to a mixing chamber, then it is mixed and then applied to the applicators.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. An apparatus for removably retaining a single use cartridge and dispensing at least one compound from the single use cartridge, the apparatus comprising:
   a. a dispensing pen having a circumferential wall with an exterior surface and an interior surface, the dispensing pen having an open rear end covered by a sealing cap, the dispensing pen having a front end wall with a front end opening extending from the front end wall, the interior surface and sealing cap surround an interior chamber which retains a ratchet operating mechanism which includes the following components, an operating pushbutton which has a rear end and an arcuate lower surface about which the operating pushbutton pivots, the circumferential wall of the dispensing pen having an opening through which the front end and a top surface wall of the operating pushbutton extend, the lower arcuate surface of the operating pushbutton rests on a pushbutton connection base having a seat on which the lower arcuate surface pivots, the pushbutton connection base having a first foot extending from a width-wise first front and underside member, the first foot member having a longitudinal body terminating in a slanted front face and a parallel oppositely disposed second foot member extending from a width-wise second front and underside member, the second foot member having a longitudinal body terminating in a slanted front face, the pushbutton connection base having a rear end with a longitudinal pivot member extending away from the rear end and against an interior location of the interior wall which serves as a connection point for the pushbutton connection base, beneath the pushbutton connection base is a longitudinal slide member having a longitudinal exterior surface with a first circumferential stop member encircling the longitudinal exterior surface at a spaced apart location from the front of the longitudinal slide member, a rear circumferential stop member located at a rear end of the longitudinal slide member and including an upper shaft holder extending away from the rear end, the upper shaft holder having a downwardly extending clip, a lower shaft holder extending away from the rear end and having an upwardly extending clip, the longitudinal exterior surface having a first flattened sidewall with a first ramp extending from an interior surface section of first circumferential stop member to adjacent a bottom longitudinal portion of the first flattened sidewall and a second flattened sidewall with a second ramp extending from an interior surface section of first circumferential stop member to adjacent a bottom longitudinal portion of the second flattened sidewall, the longitudinal slide member including an interior longitudinal generally cylindrical opening extending for the entire length of the longitudinal slide member and bounded by a longitudinal interior circumferential wall open at its front end and open at its rear end, a multi-section shaft having a first section having a smooth outer surface section extending through a length of the interior longitudinal generally cylindrical opening and for a given distance beyond the open front end adjacent a front interior wall having a cylindrical supporting arm extending interiorly toward the longitudinal slide member and having a central opening which receives and supports a front end of the multi-section shaft, a first compression spring supported by the cylindrical supporting arm at a front end and supported at a rear end by a front section of the slide member, the slide member having a front cylindrical exterior separation wall which separates the rear of the first compression spring from the pushbutton when it is depressed;
   b. a second section of the multi-section shaft having a multiplicity of adjoining ratchet teeth which extend from a given distance behind the opening at the rear end of slide member to adjacent a rear end of the multi-section shaft, the rear end of the multi-section shaft terminating in a solid plug member which in turn is received in and supported by a sealing cap, each individual ratchet tooth is in the shape of a triangle beginning with a sloped side extending at an upward slant and serving as the long straight edge of the triangle and terminating at a rear end, each triangle further formed with a vertical wall and a horizontal wall, an upper triangle and a lower triangle formed as identical mirror images of each other at a same location of the second section and respectively above and below the second section, each ratchet tooth above the second section defined to as an upper ratchet tooth with an upper vertical wall and an upper forwardly slanted surface, each ratchet tooth below the second section defined as a lower ratchet with a lower vertical wall and a lower forwardly slated surface, a second compression spring extending around the multiplicity of ratchet teeth and retained at a rear end on the solid plug member and retained at a front end on the upper shaft holder and on lower shaft holder;
   c. the exterior surface of the dispensing pen including a removable cover section adjacent the front opening leading to an interior chamber between the front opening of the dispensing pen and a front portion of the first section of the multi-section shaft, the interior chamber sized to receive a single use cartridge having a nozzle extending through the front opening and a rear end facing the front portion of the first section of the multi-section shaft;
   d. for operation of the ratchet operating mechanism, the first compression spring and the second compression spring are in their uncompressed state, the operating pushbutton is elevated in the uncompressed state, the downwardly extending clip rests on an uppermost portion of an upper forwardly slanted surface adjacent a vertical wall of an upper ratchet tooth, the upwardly extending clip rests on a lowermost portion of a lower forwardly slanted surface adjacent a vertical wall of a lower ratchet tooth, the multi-section shaft is incrementally moved toward the front end opening of the dispensing pen by a ratchet step, the operating pushbutton is pressed downwardly by pushing a top surface wall adjacent a front location of the top surface wall towards the slide member, the downwardly pressed pushbutton causes its arcuate lower surface to pivot causing the pushbutton connection base to move in the same downward direction which in turn causes the slanted front faces and of the respective first foot member and second foot member to respectively slide down the first ramp and second ramp of the slide member, when the operating pushbutton is fully pressed all the way down, the first and second foot of the pushbutton connection base respectively slide down their respective first ramp and second ramp which causes the slide member to move toward the front of the dispensing pen by a respective horizontal distance of the first ramp and the second ramp, this in turn compresses the first compression spring and advances the multi-section shaft by the a horizontal distance of a ratchet tooth which in turn compresses the second spring; when the operating pushbutton is released, the clips slide down a respective slanted surface and respectively stop at the next vertical wall of a ratchet tooth and holds the multi-sectioned shaft from moving backward, the slide member moves backwards due to the uncompressed first compression spring by the first and second foot sliding back up respective ramps which then allows the upwardly extending clip and the downwardly extending clip to respectively jump to the next respective slanted surface of the next lower ratchet tooth and upper ratchet tooth, this process continues as the operating pushbutton is pressed until the multi-section shaft is completely extended and the second compression spring is completely compressed;

e. to retract the multi-section shaft back to its original or starting point, it is necessary to disengage the upper ratchet teeth and the lower ratchet teeth from the downwardly extending ratchet tooth engagement clip and upwardly extending ratchet tooth engagement clip, surrounding the exterior surface of the exterior wall of the dispensing pen at a location between the slide member and the upper shaft holder and lower shaft holder is a rotational switch, the rotational switch is connected to a locking element attached to a cylindrical locking member physically attached to the multi-section shaft, when the rotational switch is rotated, the locking element and the cylindrical locking member also rotates, thereby causing the multi-section shaft to rotate until the clips are disengaged from the ratchet teeth, upon such disengagement, the second compression spring retracts the multi-section shaft back to its starting position, the rotational switch is rotated in the opposite direction back to its original position, the locking element and cylindrical locking member are also rotated back to their original position, thereby causing the multi-section shaft to rotate back its original position until the clips are re-engaged with the ratchet teeth to begin the starting position; and f. the dispensing pen removably retaining a single use cartridge containing at least one compound dispensed from the single use cartridge after engagement of a part of the single use cartridge by the ratchet mechanism.

2. An apparatus in accordance with claim 1, further comprising:

a. the single use cartridge received in the interior chamber of the dispensing pen includes an exterior surface which surrounds an interior circumferential wall surrounding an interior chamber and a rear opening leading to the interior chamber, a compound retained within the interior chamber, a plunger having a front interior surface aligned with the interior chamber and having sidewalls which serve as a seal against the interior circumferential wall to prevent the compound from flowing out of the rear opening, the plunger having a rear pocket, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compounds in a sealed condition within the interior chamber, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the cartridge, the exterior surface including an anti-rotation member;

b. a single pushing piston affixed onto the front of the first section of the multi-section shaft and aligned with the pocket of the plunger, the nozzle of the single use cartridge extending through the front opening of the dispensing pen, the interior chamber of the dispensing pen including an anti-rotation member engaging the anti-rotation member of the single use cartridge; and c. the ratchet operating mechanism incrementally moving the multi-section shaft toward the front opening of the dispensing pen, thereby incrementally moving the pushing piston and the plunger toward the opening in the nozzle to dispense the compound out of the single use cartridge.

3. The apparatus in accordance with claim 2, further comprising:

a. an applicator selected from the group consisting of a straight applicator, a horn shaped applicator and an applicator brush;

b. the straight applicator includes an exterior surface and an interior chamber which has a widened end with interior threads surrounding a rear opening by which the straight applicator is threaded onto the threads of the single use cartridge and then the compound is pushed out a front opening in the straight applicator;

c. the horn-shaped applicator which has an exterior wall and an interior chamber which has a rear opening and a rear interior wall having threads which are threaded onto the threads of the single use cartridge and then the compound is pushed out of a front opening in the single use cartridge;

d. the applicator brush includes interior mating threads which are threaded onto the threads of the single use cartridge and then the compound is pushed onto the applicator brush.

4. The apparatus in accordance with claim 2, further comprising: the compound is selected from the group consisting of tooth whitening compounds, dental bonding and filling compounds, adhesives such as glue, finely ground powder, jells, creams, paints, cosmetics, lipstick, non-medicated cosmetics, medicated cosmetics, and construction material compounds.

5. The apparatus in accordance with claim 1, further comprising:

a. the single use cartridge received in the interior chamber of the dispensing pen includes an exterior surface which surrounds an interior circumferential wall surrounding an interior dual chambers separated by an interior longitudinal dividing wall and a rear opening leading to the interior dual chambers, two compounds with a respective compound retained within a respective one chamber of the dual interior chambers and separated by the interior longitudinal dividing wall, a plunger having a front interior surfaces aligned with a respective one chamber and having sidewalls which serve as a seal against the interior circumferential wall to prevent the compounds from flowing out of the rear opening, the plunger having a pair of rear spaced apart pockets respectively aligned with a respective one of the dual chambers, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compounds in a sealed condition within the dual interior chambers, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the single use cartridge, the exterior surface including an anti-rotation member;

b. dual pushing pistons affixed onto the front of the first section of the multi-section shaft with a respective pushing piston aligned with a respective one of the pair of pockets of the dual plunger, the nozzle of the single use cartridge extending through the front opening of the dispensing pen, the interior chamber of the dispensing pen including an anti-rotation member engaging the anti-rotation member of the single use cartridge; and c. the ratchet operating mechanism incrementally moving the multi-section shaft toward the front opening of the dispensing pen, thereby incrementally moving the pair of plungers and the dual plunger toward the opening in the nozzle to dispense the compounds out of the single use cartridge.

6. The apparatus in accordance with claim 5, further comprising: a mixing nozzle having internal threads on an internal surface adjacent a rear open rear end of the mixing nozzle by which the mixing nozzle is threaded onto the threads of the nozzle tip of the single use cartridge, and external threads on a front surface adjacent a front end of the mixing nozzle, an interior of the mixing nozzle including a multiplicity of angular shelves and straight shelves formed into the interior of the mixing nozzle in longitudinally arranged sets so that as the compounds are driven through the mixing nozzle, the angular shelves and the straight shelves cause the compounds to mix together and go through a series of angular shelves and straight shelves to make sure that the compounds are fully mixed when the compounds are pushed to a front opening in the mixing nozzle.

7. The apparatus in accordance with claim 6, further comprising:

a. an applicator selected from the group consisting of a straight applicator, a horn shaped applicator and an applicator brush;

b. the straight applicator includes an exterior surface and an interior chamber which has a widened end with interior threads surrounding a rear opening by which the straight applicator is threaded onto the exterior threads of the mixing nozzle so that compounds are pushed out of the single use cartridge into the mixing nozzle and then mixed compounds are pushed out of the mixing nozzle into the straight applicator and then pushed out a front opening in the straight applicator;

c. the horn-shaped applicator which has an exterior wall and an interior chamber which has a rear opening and a rear interior wall having threads which are threaded onto the exterior threads of the mixing nozzle so that compounds are pushed out of the single use cartridge into the mixing nozzle and then mixed compounds are pushed out of the mixing nozzle into the horn shaped applicator which is bent at an angle so that the compounds are pushed out of a front opening in the horn shaped applicator; and d. the applicator brush includes interior mating threads which are threaded onto the exterior threads of the mixing nozzle so that the compounds are pushed out of the single use cartridge into the mixing nozzle and then mixed compounds are pushed out of the mixing nozzle onto the applicator brush.

8. The apparatus in accordance with claim 5, further comprising: each of the compounds are respectively selected from the group consisting of tooth whitening compounds, dental bonding and filling compounds, adhesives such as glue, finely ground powder, jells, creams, paints, cosmetics, lipstick, non-medicated cosmetics, medicated cosmetics, and construction material compounds.

9. An apparatus for removably retaining a single use cartridge and dispensing at least one compound from the single use cartridge, the apparatus comprising:

a. a dispensing pen having a circumferential wall with an exterior surface and an interior surface, the dispensing pen having an open rear end covered by a sealing cap, the dispensing pen having a front end wall with a front end opening extending from the front end wall, the interior surface and sealing cap surround an interior chamber which retains a ratchet operating mechanism which includes the following components, an operating pushbutton which has a rear end and an arcuate lower surface about which the operating pushbutton pivots, the circumferential wall of the dispensing pen having an opening through which the front end and a top surface wall of the operating pushbutton extend, the lower arcuate surface of the operating pushbutton rests on a pushbutton connection base having a seat on which the lower arcuate surface pivots, the pushbutton connection base having a first foot extending from a width-wise first front and underside member, the first foot member having a longitudinal body terminating in a slanted front face and a parallel oppositely disposed second foot member extending from a width-wise second front and underside member, the second foot member having a longitudinal body terminating in a slanted front face, the pushbutton connection base having a rear end with a longitudinal pivot member extending away from the rear end and against an interior location of the interior wall which serves as a connection point for the pushbutton connection base, beneath the pushbutton connection base is a longitudinal slide member having a longitudinal exterior surface with a first circumferential stop member encircling the longitudinal exterior surface at a spaced apart location from the front of the longitudinal slide member, a rear circumferential stop member located at a rear end of the longitudinal slide member and including an upper shaft holder extending away from the rear end, the upper shaft holder having a downwardly extending clip, a lower shaft holder extending away from the rear end and having an upwardly extending clip, the longitudinal exterior surface having a first flattened sidewall with a first ramp extending from an interior surface section of first circumferential stop member to adjacent a bottom longitudinal portion of the first flattened sidewall and a second flattened sidewall with a second ramp extending from an interior surface section of first circumferential stop member to adjacent a bottom longitudinal portion of the second flattened sidewall, the longitudinal slide member including an interior longitudinal generally cylindrical opening extending for the entire length of the longitudinal slide member and bounded by a longitudinal interior circumferential wall open at its front end and open at its rear end, a multi-section shaft having a first section having a smooth outer surface section extending through a length of the interior longitudinal generally cylindrical opening and for a given distance beyond the open front end adjacent a front interior wall having a cylindrical supporting arm extending interiorly toward the longitudinal slide member and having a central opening which receives and supports a front end of the multi-section shaft, a first compression spring supported by the cylindrical supporting arm at a front end and supported at a rear end by a front section of the slide member, the slide member having a front cylindrical exterior separation wall which separates the rear of the first compression spring from the pushbutton when it is depressed;

b. a second section of the multi-section shaft having a multiplicity of adjoining ratchet teeth which extend from a given distance behind the opening at the rear end of slide member to adjacent a rear end of the multi-section shaft, the rear end of the multi-section shaft terminating in a solid plug member which in turn is received in and supported by a sealing cap, each individual ratchet tooth is in the shape of a triangle beginning with a sloped side extending at an upward slant and serving as the long straight edge of the triangle and terminating at a rear end, each triangle further formed with a vertical wall and a horizontal wall, an upper triangle and a lower triangle formed as identical mirror images of each other at a same location of the second section and respectively above and below the second section, each ratchet tooth above the second section defined as an upper ratchet tooth with an upper vertical wall and an upper forwardly slanted surface, each ratchet tooth below the second section defined as a lower ratchet with a lower vertical wall and a lower forwardly slated surface, a second compression spring extending around the multiplicity of ratchet teeth and retained at a rear end on the solid plug member and retained at a front end on the upper shaft holder and on lower shaft holder;

c. the dispensing pen including a front section having a threaded exterior surface with mating threads thereon, a front of the first section of the multi-section shaft positioned to protrude through the front end opening of the dispensing pen and located forwardly of the front section of the dispensing pen;
the front section and mating threads sized to receive a single use cartridge having interior threads which are retained by the mating threads of the front section to retain the single use cartridge on and in front of the dispensing pen with the single use cartridge having a rear end facing the front section of the dispensing pen;

d. for operation of the ratchet operating mechanism, the first compression spring and the second compression spring are in their uncompressed state, the operating pushbutton is elevated in the uncompressed state, the downwardly extending clip rests on an uppermost portion of an upper forwardly slanted surface adjacent a vertical wall of an upper ratchet tooth, the upwardly extending clip rests on a lowermost portion of a lower forwardly slanted surface adjacent a vertical wall of a lower ratchet tooth, the multi-section shaft is incrementally moved toward the front end opening of the dispensing pen by a ratchet step, the operating pushbutton is pressed downwardly by pushing a top surface wall adjacent a front location of the top surface wall towards the slide member, the downwardly pressed pushbutton causes its arcuate lower surface to pivot causing the pushbutton connection base to move in the same downward direction which in turn causes the slanted front faces and of the respective first foot member and second foot member to respectively slide down the first ramp and second ramp of the slide member, when the operating pushbutton is fully pressed all the way down, the first and second foot of the pushbutton connection base respectively slide down their respective first ramp and second ramp which causes the slide member to move toward the front of the dispensing pen by a respective horizontal distance of the first ramp and the second ramp, this in turn compresses the first compression spring and advances the multi-section shaft by the a horizontal distance of a ratchet tooth which in turn compresses the second spring; when the operating pushbutton is released, the clips slide down a respective slanted surface and respectively stop at the next vertical wall of a ratchet tooth and holds the multi-sectioned shaft from moving backward, the slide member moves backwards due to the uncompressed first compression spring by the first and second foot sliding back up respective ramps which then allows the upwardly extending clip and the downwardly extending clip to respectively jump to the next respective slanted surface of the next lower ratchet tooth and upper ratchet tooth, this process continues as the operating pushbutton is pressed until the multi-section shaft is completely extended and the second compression spring is completely compressed;

e. to retract the multi-section shaft back to its original or starting point, it is necessary to disengage the upper ratchet teeth and the lower ratchet teeth from the downwardly extending ratchet tooth engagement clip and upwardly extending ratchet tooth engagement clip, surrounding the exterior surface of the exterior wall of the dispensing pen at a location between the slide member and the upper shaft holder and lower shaft holder is a rotational switch, the rotational switch is connected to a locking element attached to a cylindrical locking member physically attached to the multi-section shaft, when the rotational switch is rotated, the locking element and the cylindrical locking member also rotates, thereby causing the multi-section shaft to rotate until the clips are disengaged from the ratchet teeth, upon such disengagement, the second compression spring retracts the multi-section shaft back to its starting position, the rotational switch is rotated in the opposite direction back to its original position, the locking element and cylindrical locking member are also rotated back to their original position, thereby causing the multi-section shaft to rotate back its original position until the clips are re-engaged with the ratchet teeth to begin the starting position; and f. the dispensing pen removably retaining a single use cartridge containing at least one compound dispensed from the single use cartridge.

10. The apparatus in accordance with claim 9, further comprising:
  a. the single use cartridge retained in front of the dispensing pen includes an exterior surface which surrounds an interior circumferential wall surrounding an interior chamber and a rear opening leading to the front of the front section of the multi-sectioned shaft, compound retained within the interior chamber, a plunger having a front interior surface aligned with the interior chamber and having sidewalls which serve as a seal against the interior circumferential wall to prevent the compound from flowing out of the rear opening, the plunger having a rear pocket, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compound in a sealed condition within the interior chamber, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the single use cartridge, the piercing tooth is used to penetrate the frangible seal so that the nozzle tip is opened to enable the compound to be dispensed from the interior of the cartridge;
  b. a single pushing piston affixed onto the front of the first section of the multi-section shaft and aligned with the pocket of the plunger; and
  c. the ratchet operating mechanism incrementally moving the multi-section shaft toward the pocket of the single use cartridge, thereby incrementally moving the pushing piston and the plunger toward the opening in the nozzle to dispense the compound out of the single use cartridge.

11. The apparatus in accordance with claim 10, further comprising:
  a. an applicator selected from the group consisting of a straight applicator, a horn shaped applicator and an applicator brush;
  b. the straight applicator includes an exterior surface and an interior chamber which has a widened end with interior threads surrounding a rear opening by which the straight applicator is threaded onto the threads of the single use cartridge and then the compound is pushed out a front opening in the straight applicator;
  c. the horn-shaped applicator which has an exterior wall and an interior chamber which has a rear opening and a rear interior wall having threads which are threaded onto the threads of the single use cartridge and then the compound is pushed out of a front opening in the single use cartridge; and
  d. the applicator brush includes interior mating threads which are threaded onto the threads of the single use cartridge and then the compound is pushed onto the applicator brush.

12. The apparatus in accordance with claim 10, further comprising: the compound is selected from the group consisting of tooth whitening compounds, dental bonding and filling compounds, adhesives such as glue, finely ground powder, jells, creams, paints, cosmetics, lipstick, non-medicated cosmetics, medicated cosmetics, and construction material compounds.

13. The apparatus in accordance with claim 9, further comprising:
  a. the single use cartridge retained in front of the dispensing pen includes an exterior surface which surrounds an interior circumferential wall surrounding interior dual chambers and a rear opening leading to the front of the front section of the multi-sectioned shaft, the interior dual chambers separated by an interior longitudinal dividing wall and a rear opening leading to the interior dual chambers, two compounds with a respective compound retained within a respective one chamber of the dual interior chambers and separated by the interior longitudinal dividing wall, a plunger having a front interior surfaces aligned with a respective one chamber and having sidewalls which serve as a seal against the interior circumferential wall to prevent the compounds from flowing out of the rear opening, the plunger having a pair of rear spaced apart pockets respectively aligned with a respective one of the dual chambers, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compounds in a sealed condition within the dual interior chambers, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the single use cartridge, the exterior surface including an anti-rotation member;
  b. dual pushing pistons affixed onto the front of the first section of the multi-section shaft with a respective pushing piston aligned with a respective one of the pair of pockets of the dual plunger; and
  c. the ratchet operating mechanism incrementally moving the multi-section shaft toward the respective pockets of the dual plunger, thereby incrementally moving the pair of plungers and the dual plunger toward the opening in the nozzle to dispense the compounds out of the single use cartridge.

14. The apparatus in accordance with claim 13, further comprising: a mixing nozzle having internal threads on an internal surface adjacent a rear open rear end of the mixing nozzle by which the mixing nozzle is threaded onto the threads of the nozzle tip of the single use cartridge, and external threads on a front surface adjacent a front end of the mixing nozzle, an interior of the mixing nozzle including a multiplicity of angular shelves and straight shelves formed into the interior of the mixing nozzle in longitudinally arranged sets so that as the compounds are driven through the mixing nozzle, the angular shelves and the straight shelves cause the compounds to mix together and go through a series of angular shelves and straight shelves to make sure that the compounds are fully mixed when the compounds are pushed to a front opening in the mixing nozzle.

15. The apparatus in accordance with claim 14, further comprising:
  a. an applicator selected from the group consisting of a straight applicator, a horn shaped applicator and an applicator brush;
  b. the straight applicator includes an exterior surface and an interior chamber which has a widened end with interior threads surrounding a rear opening by which the straight applicator is threaded onto the exterior threads of the mixing nozzle so that compounds are pushed out of the single use cartridge into the mixing nozzle and then mixed compounds are pushed out of the mixing nozzle into the straight applicator and then pushed out a front opening in the straight applicator;
  c. the horn-shaped applicator which has an exterior wall and an interior chamber which has a rear opening and a rear interior wall having threads which are threaded onto the exterior threads of the mixing nozzle so that compounds are pushed out of the single use cartridge into the mixing nozzle and then mixed compounds are pushed out of the mixing nozzle into the horn shaped applicator which is bent at an angle so that the compounds are pushed out of a front opening in the horn shaped applicator; and
  d. the applicator brush includes interior mating threads which are threaded onto the exterior threads of the mixing nozzle so that the compounds are pushed out of the single use cartridge into the mixing nozzle and then mixed compounds are pushed out of the mixing nozzle onto the applicator brush.

16. The apparatus in accordance with claim 13, further comprising: each of the compounds are respectively selected from the group consisting of tooth whitening tooth whitening compounds, dental bonding and filling compounds, adhesives such as glue, finely ground powder, jells, creams, paints, cosmetics, lipstick, non-medicated cosmetics, medicated cosmetics, and construction material compounds.

* * * * *